(12) United States Patent
Alfaro-Lopez et al.

(10) Patent No.: US 9,217,022 B2
(45) Date of Patent: Dec. 22, 2015

(54) GLP-1 RECEPTOR AGONIST COMPOUNDS HAVING STABILIZED REGIONS

(75) Inventors: Josue Alfaro-Lopez, San Diego, CA (US); Abhinandini Sharma, San Diego, CA (US); Christopher J. Soares, Wilmington, DE (US); Eugene Coats, Wilmington, DE (US); Soumitra S. Ghosh, Wilmington, DE (US)

(73) Assignees: AstraZeneca Pharmaceuticals LP, Wilmington, DE (US); Amylin Pharmaceuticals, LLC, Wilmington, DE (US)

(*) Notice: Subject to any disclaimer, the term of this patent is extended or adjusted under 35 U.S.C. 154(b) by 43 days.

(21) Appl. No.: 13/812,445

(22) PCT Filed: Jul. 27, 2011

(86) PCT No.: PCT/US2011/045614
§ 371 (c)(1),
(2), (4) Date: Apr. 4, 2013

(87) PCT Pub. No.: WO2012/015975
PCT Pub. Date: Feb. 2, 2012

(65) Prior Publication Data
US 2013/0184203 A1    Jul. 18, 2013

Related U.S. Application Data

(60) Provisional application No. 61/368,522, filed on Jul. 28, 2010.

(51) Int. Cl.
*C07K 14/605* (2006.01)
*A61K 38/00* (2006.01)

(52) U.S. Cl.
CPC ............ *C07K 14/605* (2013.01); *A61K 38/00* (2013.01); *Y02E 50/343* (2013.01)

(58) Field of Classification Search
CPC ............................. A61K 38/26; C07K 14/605
See application file for complete search history.

(56) References Cited

U.S. PATENT DOCUMENTS

| | | |
|---|---|---|
| 6,620,910 B1 | 9/2003 | Calas et al. |
| 7,816,324 B2 * | 10/2010 | Ahn et al. ............ 514/7.2 |
| 2006/0183677 A1 | 8/2006 | Young et al. |
| 2007/0238669 A1 | 10/2007 | Haque et al. |
| 2010/0184645 A1 * | 7/2010 | Verdine et al. ............ 514/9 |

FOREIGN PATENT DOCUMENTS

| | | |
|---|---|---|
| WO | 09907404 A1 | 2/1999 |
| WO | 2008112941 A1 | 9/2008 |
| WO | WO 2008/112938 A2 | 9/2008 |
| WO | 2010043047 A1 | 4/2010 |
| WO | WO 2010/083215 A2 | 7/2010 |
| WO | WO 2010/120476 A2 | 10/2010 |
| WO | WO 2012/006598 A2 | 1/2012 |

OTHER PUBLICATIONS

Andersen et al. "Medium-Dependence of the Secondary Structure of Exendin-4 and Glucagon-like-peptide-1," Bioorganic & Medicinal Chemistry 10 (2002) 79-85.*
Ahn, Jung-Mo et al., "Rational Design of Peptidomimetics for Class B GPCRs: Potent Non-Peptide GLP-1 Receptor Agonist", Advances in Experimental Medicine and Biology 2009, vol. 611 (2009) pp. 125-126.
Han, Sun-Young et al., "Facile Synthesis of Glucagon-like Peptide-1 (GLP-1) Mimetics" Advances in Experimental Medicine and Biology 2009, vol. 611, (2009) pp. 119-120.
Ahn, Jung Mo et al., "Facile Synthesis of Benzamides to Mimic an Alpha-Helix", Tetrahedron Letters, Pergamon, GB, vol. 48, pp. 3543-3547, No. 20, (Apr. 19, 2007).
Shaginian, Alex et al., "Design, Synthesis, and Evaluation of an Alpha-Helix Mimetic Library Targeting Protein—Protein Interactions", Journal of the American Chemical Society, vol. 131, No. 15, pp. 5564-5572 (Apr. 22, 2009).
G. H. Bird, et al., "Hydrocarbon Double-Stapling Remedies the Proteolytic Instability of a Lengthy Peptide Therapeutic", Proceedings of the National Academy of Sciences, vol. 107, No. 32 (Jul. 21, 2010).
Supplementary European Search Report for EP 11 81 3145 dated Jan. 17, 2014.
Plante et al., "Oligobenzamide proteomimetic inhibitors of the p53-hDM2 protein-protein interaction," Chem. Commun. 2009, 5091-5093.

* cited by examiner

*Primary Examiner* — Christina Bradley
(74) *Attorney, Agent, or Firm* — Mintz Levin Cohn Ferris Glovsky and Popeo, P.C.

(57) ABSTRACT

The disclosure provides GLP-1 receptor agonist compounds having stabilized regions corresponding to alpha-helical regions of the natural peptide compounds. The disclosure also provides benzamide-containing exendin-4 analogs and alkene-constrained exendin-4 analogs, both of which have stabilized regions corresponding to alpha-helical regions of exendin-4.

2 Claims, 2 Drawing Sheets

GLP-1 RECEPTOR AGONIST COMPOUNDS HAVING STABILIZED REGIONS

CROSS-REFERENCE TO RELATED APPLICATIONS

This application is a national phase of International Application No. PCT/US11/45614, filed Jul. 27, 2011, which claims priority to U.S. Application No. 61/368,522 filed Jul. 28, 2010, the disclosure of each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Sep. 19, 2011, is named 0246W01.txt and is 29,122 bytes in size.

FIELD

The disclosure is directed to glucagon-like peptide-1 (GLP-1) receptor agonist compounds having stabilized regions, pharmaceutical compositions containing the GLP-1 receptor agonist compounds, therapeutic treatments using the GLP-1 receptor agonist compounds, and methods for making the GLP-1 receptor agonist compounds.

BACKGROUND

Peptides and proteins play critical roles in the regulation of biological processes. Peptides, for example, play a regulatory role as hormones and inhibitors, and are also involved in immunological recognition. The significant biological role of peptides makes it important to understand their interactions with the receptors to which they bind.

The determination of the receptor-bound conformation of a peptide is invaluable for the rational design of peptide analogs. Because peptides are highly flexible molecules, the structures of which are strongly influenced by the environment in which they reside, the peptides themselves are generally not useful for determining their receptor-bound conformation. Therefore, it is necessary to perform structure-function studies in a systematic way to provide information about the specific amino acid residues and functional groups in peptides that are important to biological activity. Studies of this nature can utilize conformationally constrained peptide mimetics. For example, Hruby, *Trends Pharmacol. Sci.*, 8:336-339 (1987) suggests that conformational constraints can provide information about the different requirements that a receptor has for a ligand to be an agonist or antagonist.

Peptide mimetics or peptidomimetics are structures which serve as appropriate substitutes for peptides and/or amino acids in interactions with receptors and enzymes. The development of rational approaches for discovering peptide mimetics is a major goal of medicinal chemistry. Such development has been attempted both by empirical screening approaches and specific synthetic design. Specific design of peptide mimetics has utilized peptide backbone modifications, chemical mimics of peptide secondary structures and covalent constraints on the peptide parent to facilitate such peptide secondary structures.

Alpha helices present the side chains of the residues thereof along a rod-like helical structure. Approximately 3.6 amino acid residues make up a single turn of an alpha-helix. Thus, side chains that are adjacent in space form a "side" of an alpha-helix with residues which occur every three to four residues along the linear amino acid sequence. As customary in the art, this spacing can be referred to as "i, i+3/i+4, i+7" and the like to indicate that the side chains of residues offset from residue "i" lie approximately along a side of the alpha helix, in spatial proximity. The term "face" in the context of alpha helices is synonymous with the term "side." It is believed that the i, i+3/i+4 and i+7 residues can make crucial contacts with a target protein, and that such contacts constitute the majority of binding energy. Fairlie et al., *Curr. Med. Chem.*, 5:29 (1998). The alpha-helix conformation is stabilized by steric interactions along the backbone as well as hydrogen bonding interactions between the backbone amide carbonyls and NH groups of each amino acid. The side chains of an alpha helix project with well known distances and angular relationships. Jain et al., *Mol. Divers.*, 8:89-100 (2004).

The syntheses of peptidomimetics having a stabilized alpha-helical conformation have been achieved by introducing synthetic templates into the peptidic, by using β-hairpin mimetics, by using β-peptide sequences, and by using unnatural oligomers with discrete folding propensities. Small synthetic molecules able to mimic the surfaces of constrained peptides offer the advantage of improved stability, lower molecular weight and in some cases better bioavailability. Synthetic small molecules that adopt various well-defined secondary structures are well-documented in the art. A variety of strategies to enhance the propensity for alpha helix formation in peptides are known in the art. Exemplary methods include side-chain constraints, capping, and nonnatural amino acid substitutions.

Another class of constraints for alpha helices employ ring closing metathesis (RCM) reactions to form side chain to side chain bridges which incorporate a double bond (e.g., alkenylenyl bridges) or no double bond (e.g., alkylenyl bridges). The discovery of the olefin metathesis reaction provided a convenient path for synthesis and cleavage of carbon-carbon bonds under mild conditions. In particular, the use of RCM reactions catalyzed by ruthenium complexes has become a popular method for the formation of alkenylenyl bridged structures in organic syntheses. Application of this method to amino acids bearing unsaturated side chains (e.g., allylglycine, homoallylglycine and the like) and located in strategic positions of the peptide motif allows the preparation of cyclic peptides by solid-phase peptide synthetsis (SPPS) methods.

There is a need in the art for new GLP-1 receptor agonist compounds that have good stability, resistance to degradation, and good glucagon-like peptide-1 (GLP-1) receptor binding activity and in vivo glucose lowering activity and that are useful for treating diabetes and reducing body weight. To solve these needs, the disclosure herein provides, among other things, GLP-1 receptor agonist compounds having stabilized alpha-helical regions.

SUMMARY

The alpha-helical conformation is adopted by 40% of all amino acid residues in proteins and, according to the helix-coil transition theory, alpha-helixes composed of 10 or fewer amino acids are expected to be essentially unstable due to low nucleation probability. In the case of GLP-1 receptor agonists, such as exendin-4 and GLP-1(7-37), the alpha-helix represents an important sequence-selective recognition motif. The alpha-helical receptor binding region in exendin-4 is general at positions 9-30, while the alpha-helical receptor binding region in GLP-1(7-37) is at positions 15-37 inclusive. The helical character of exendin-4 and GLP-1(7-37) expands about 20 amino acids.

The disclosure provides GLP-1 receptor agonist compounds, such as exendin-4, having alpha-helix mimetics or alpha-helix stabilization that can retain in vitro and in vivo activity. This provides a better understanding of key side chain residues that may be involved in the molecular recognition event and can be used to develop smaller GLP-1 receptor agonist compounds having superior metabolic stability and enhanced properties, such that they may be used in oral formulations. This also provides new GLP-1 receptor agonist compounds useful for treating numerous diseases and disorders.

The disclosure provides benzamide-containing peptide compounds comprising an amino acid sequence having at least 50% sequence identity to Formula (I):

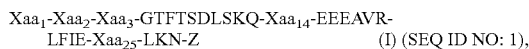

Xaa$_1$-Xaa$_2$-Xaa$_3$-GTFTSDLSKQ-Xaa$_{14}$-EEEAVR-LFIE-Xaa$_{25}$-LKN-Z    (I) (SEQ ID NO: 1), wherein Formula (I) has at least one benzamide moiety that mimics the side chain of one or more physiologic amino acids; and wherein Xaa$_1$, Xaa$_2$, Xaa$_3$, Xaa$_{14}$, Xaa$_{25}$, and Z are as defined herein. In one embodiment, the benzamide-containing peptide compounds have an amino acid sequence having at least 80%, at least 90%, or at least 95% sequence identity with Formula (I). The disclosure provides pharmaceutical composition comprising these benzamide-containing compounds. The disclosure provides methods of treating numerous diseases (e.g., diabetes) using the benzamide-containing compounds and the pharmaceutical compositions containing them.

The disclosure provides constrained alkene peptide compounds comprising an amino acid sequence having at least 50% sequence identity to Formula (IV):

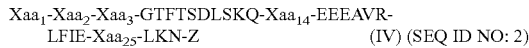

Xaa$_1$-Xaa$_2$-Xaa$_3$-GTFTSDLSKQ-Xaa$_{14}$-EEEAVR-LFIE-Xaa$_{25}$-LKN-Z    (IV) (SEQ ID NO: 2)

wherein at least one pair of amino acid residues in the peptide compound are linked by an alkenylenyl bridge or an alkylenyl bridge; and wherein Xaa$_1$, Xaa$_2$, Xaa$_3$, Xaa$_{14}$, Xaa$_{25}$, and Z are as defined herein. In one embodiment, the constrained alkene peptide compounds have an amino acid sequence having at least 80%, at least 90%, or at least 95% sequence identity with Formula (IV). The disclosure provides pharmaceutical composition comprising these constrained alkene compounds. The disclosure provides methods of treating numerous diseases (e.g., diabetes) using the constrained alkene compounds and the pharmaceutical compositions containing them.

The disclosure provides methods for the solid-phase synthesis of the benzamide-containing peptide compounds described herein. A resin-bound reagent having a free amine is reacted with a substituted phenyl having a side chain surrogate moiety, a free carboxylic acid and a nitro moiety thereby forming a resin-bound substituted benzamidyl. The nitro moiety is reduced to form a free amine thereby forming a resin-bound substituted benzamidyl having a free amine, which is therefore available for additional solid-phase reaction.

BRIEF DESCRIPTION OF THE FIGURES

For purposes of the Figures and the Examples they represent, Cmpd T1 is HaPGTFTSDLSKQLEEEAVRLFIEF-LKN-NH$_2$ (SEQ ID NO: 3); wherein the lower case "a" in position 2 is dAla; and Compound T2 is HGEGTFTSDL-SKQLEEEAVRLFIEFLKN-NH$_2$ (SEQ ID NO: 4). Throughout the specification, the lower case "a" in a sequence represented by single letter amino acid abbreviations is dAla.

DETAILED DESCRIPTION

Figure 1:
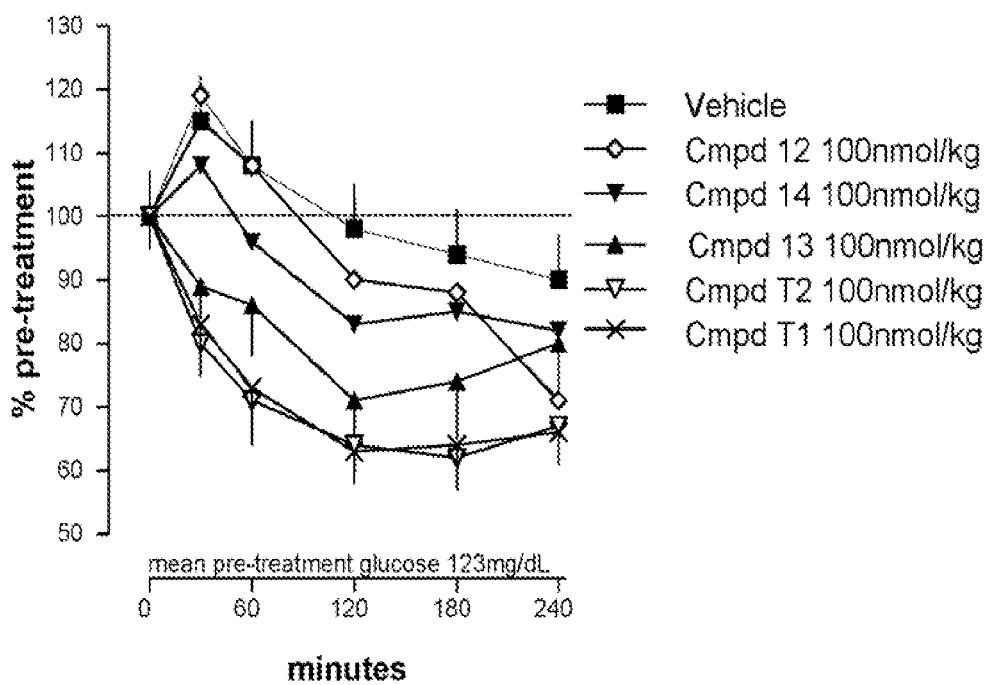
FIG. 1 depicts the time course of blood glucose concentration as a percentage of pre-treatment levels, for certain benzamide-containing compounds described herein. The pretreatment glucose concentration was 123 mg/dL. Points represent mean±s.d. (standard deviation. Compounds were injected IP (100 nmol/kg) at t=0 immediately following baseline sample into 2-hr fasted NIH/Swiss mice. Samples were taken at t=30, 60, 120, 180 and 240 min. Blood glucose was measured using One Touch® Ultra® (LifeScan, Inc., Milpitas, Calif.) following manufacturer's instructions. Legend: Vehicle (closed box); Cmpd 12 (open diamond); Cmpd 14 (close triangle tip down); Cmpd 13 (closed triangle tip up); Cmpd T2 (open triangle); Cmpd T1 (cross).

The abbreviations used herein have their conventional meaning within the chemical and biological arts. The chemical structures and formulae set forth herein are constructed according to the standard rules of chemical valency known in the chemical arts. Where there are differences between the conventional meaning and the definitions described herein, the definitions described herein should prevail.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one, two, three, four, five, six, seven, eight, nine, and ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds (i.e., "alkenyl") or triple bonds (i.e., "alkynyl"). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butyryl, and the higher homologs and isomers. An alkoxy is an alkyl attached to the remainder of the molecule via an oxygen linker (—O—). An alkylthio is an alkyl attached to the remainder of the molecule via a sulfur linker (—S—).

The terms "alkylene" and "alkylenyl" alone or as part of another substituent mean a divalent radical derived from an alkyl, as exemplified, but not limited by, —CH$_2$CH$_2$CH$_2$CH$_2$—. Typically, an alkyl (or alkylene) group will have from 1 to 24 carbon atoms, preferably 10 or fewer carbon atoms, more preferably 4 or fewer carbon atoms. A "lower alkyl" or "lower alkylene" is a shorter chain alkyl or alkylene group, generally having eight or fewer carbon atoms. The terms "alkenylene" and "alkenylenyl" alone or as part of another substituent, means a divalent radical derived from an alkene.

The term "heteroalkyl," by itself or in combination with another term, means, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

The terms "heteroalkylene" and "heteroalkylenyl" alone or as part of another substituent, means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'- represents both —C(O)$_2$R'- and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" or "cycloalkylenyl," and a "heterocycloalkylene" or "heterocycloalkylenyl," alone or as part of another substituent, means a divalent radical derived from a cycloalkyl and heterocycloalkyl, respectively.

The terms "halo" or "halogen," by themselves or as part of another substituent, mean a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

The term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" means an oxygen that is double bonded to a carbon atom.

The term "alkylsulfonyl" means a moiety having the formula —S(O$_2$)—R', where R' is an alkyl group as defined above. R' may have a specified number of carbons (e.g., "C$_1$-C$_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O) NR''R''', —NR''C(O)$_2$R', —NR—C(NR'R''R''')=NR''', —NR—C(NR'R')=NR''', —S(O)R', —S(O)$_2$R', —S(O)$_2$NR'R'', —NRSO$_2$R', —CN, and —NO$_2$ in a number ranging from zero to (2 m'+1), where m' is the total number of carbon atoms in such radical. R', R'', R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R'', R''', and R'''' group when more than one of these groups is present. When R' and R'' are attached to the same nitrogen atom, they can be combined with the nitrogen atom to form a 4-, 5-, 6-, or 7-membered ring. For example, —NR'R'' includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR''', —NR—C(NR'R')=NR''', —S(O)R', —S(O)$_2$R', —S(O)$_2$NR'R'', —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R'', R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U-, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B-, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'-(C''R''')$_d$—, where s and d are independently integers of from 0 to 3, and X' is —O—, —NR'—, —S—, —S(O)—, —S(O)$_2$—, or —S(O)$_2$NR'—. The substituents R, R', R'', and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

The terms "heteroatom" or "ring heteroatom" mean oxygen (O), nitrogen (N), sulfur (S), phosphorus (P), and silicon (Si).

A "substituent group" means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The compounds described herein may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers, and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

"Analog" as used herein in the context of peptides refers to a compound that has insertions, deletions and/or substitutions of amino acids relative to a parent compound. An analog may have superior stability, solubility, efficacy, half-life, and the like. In some embodiments, an analog is a compound having at least 50%, at least 55%, at least 60%, at least 65%, at least 70%, at least 75%, at least 80%, at least 85%, at least 90%, at least 95%, at least 98%, sequence identity to the parent compound. In one embodiment, the parent compound is exendin-4.

A "derivative" is defined as a molecule having the amino acid sequence of a parent or analog thereof, but additionally having a chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, constrained alkyls (e.g. branched, cyclic, fused, adamantyl) and N-acyl modifications. Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Furthermore, one or more side groups, or terminal groups, may be protected by protective groups known to the ordinarily-skilled synthetic chemist. The alpha-carbon of an amino acid may be mono- or dimethylated.

Derivatives of the agonists and analogs are also included within the methods provided in which the stereochemistry of individual amino acids may be inverted from (L)/S to (D)/R at one or more specific sites. Also included within the methods provided are the agonists and analogs modified by glycosylation of Asn, Ser and/or Thr residues.

The terms "identity," "sequence identity" and the like in the context of comparing two or more nucleic acids or peptide sequences, refer to two or more sequences or subsequences that are the same or have a specified percentage of amino acid residues or nucleotides that are the same (i.e., about 50% identity, preferably 50%, 55%, 60%, 65%, 70%, 75%, 80%, 85%, 90%, 91%, 92%, 93%, 94%, 95%, 96%, 97%, 98%, 99% over a specified region, when compared and aligned for maximum correspondence over a comparison window or designated region) as measured using a sequence comparison algorithms as known in the art, for example BLAST or BLAST 2.0. This definition includes sequences that have deletions and/or additions, as well as those that have substitutions, as well as naturally occurring, e.g., polymorphic or allelic variants, and man-made variants. In preferred algorithms, account is made for gaps and the like, as known in the art. For sequence comparison, typically one sequence acts as a reference sequence, to which test sequences are compared. When using a sequence comparison algorithm, test and reference sequences are entered into a computer, subsequence coordinates are designated if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters. Optimal alignment of sequences for comparison can be conducted, e.g., by the local homology algorithm of Smith & Waterman, *Adv. Appl. Math.*, 2:482 (1981), by the homology alignment algorithm of Needleman & Wunsch, *J. Mol. Biol.*, 48:443 (1970), by the search for similarity method of Pearson & Lipman, *Proc. Nat'l. Acad. Sci., USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. See, e.g., Current Protocols in Molecular Biology (Ausubel et al., eds. 1995 supplement)). Preferred examples of algorithms that are suitable for determining percent sequence identity and sequence similarity include the BLAST and BLAST 2.0 algorithms, which are described in Altschul et al., *Nuci. Acids Res.*, 25:3389-3402 (1977) and Altschul et al., *J. Mol. Biol.* 215:403-410 (1990). BLAST and BLAST 2.0 are used, as known in the art, to determine percent sequence identity for the nucleic acids and proteins of the invention. Software for performing BLAST analyses is publicly available through the web site of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., Id.). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Nat. Acad. Sci. USA,* 89:10915 (1989)) alignments (B) of 50, expectation (E) of 10, M=5, N=−4, and a comparison of both strands.

To determine the percent identity or similarity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same or similar amino acid residue or nucleotide as the corresponding position in the second sequence, then the molecules are identical or similar at that position. The percent identity or similarity between the two sequences is a function of the number of identical or similar positions shared by the sequences (i.e., % identity=# of identical positions/total # of positions (e.g., overlapping positions)×100). The similarity of two amino acids can be assessed by a variety of methods known in the art. For example, nonpolar neutral residues (e.g., Ala, Cys, Gly, Ile, Leu, Met, Phe, Pro, Trp, Val) can be considered similar, as can in turn acidic charged polar (e.g., Glu, Asp), basic charged polar (e.g., Arg, His, Lys) and neutral polar (e.g., Asn, Gln, Ser, Thr, Tyr) residues.

Both identity and similarity may be readily calculated. For example, in calculating percent identity, only exact matches may be counted, and global alignments may be performed as opposed to local alignments. Methods commonly employed to determine identity or similarity between sequences include, e.g., those disclosed in Carillo et al., 1988, SIAM *J. Applied Math.* 48:1073. Exemplary methods to determine identity are designed to give the largest match between the sequences tested. Exemplary methods to determine identity and similarity are also provided in commercial computer programs. A particular example of a mathematical algorithm utilized for the comparison of two sequences is the algorithm of Karlin et al., 1990, *Proc. Natl. Acad. Sci. USA* 87:2264-2268, and as modified e.g., as in Karlin et al., 1993, *Proc. Natl. Acad. Sci. USA* 90:5873-5877. Such an algorithm is incorporated into the NBLAST and XBLAST programs of Altschul et al., 1990, *J. Mol. Biol.* 215:403-410. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search, which detects distant relationships between molecules. When utilizing BLAST, Gapped BLAST, and PSI-Blast programs, the default parameters of the respective programs (e.g., XBLAST and NBLAST) can be used, as known in the art. Additionally, the FASTA method (Atschul et al., 1990, Id.) can be used. Another particular example of a mathematical algorithm useful for the comparison of sequences is the algorithm of Myers et al., 1988, CABIOS 4:11-17. Such an algorithm is incorporated into the ALIGN program (version 2.0), which is part of the GCG sequence alignment software package (Devereux et al., 1984, *Nucleic Acids Res.* 12(1):387). Percent identity can be determined by analysis with the AlignX® module in Vector NTI® (Invitrogen; Carlsbad Calif.).

"Patient" refers to warm-blooded animals. Patients include humans; companion animals (e.g., dogs, cats); farm animals (e.g., cows, horses, sheep, pigs, goats); wild animals; and the like. In one embodiment, the patient is a human. In one embodiment, the patient is a human having type 2 diabetes. In one embodiment, the patient is an obese human having type 2 diabetes.

The terms "peptide" and "polypeptide" in the context of components of the peptide conjugates described herein are synonymous. The term "peptide" refers in the customary sense to a polymer of amino acids connected by amide bonds. The terms "des-amino acid," "des-AA," "desLys" and the like refer to the absence of the indicated amino acid. An amino acid being "absent" means that the residues (or functionalities) formerly attached at the N-terminal and C-terminal side of the absent amino acid have become bonded together.

The terms "side chain surrogate" and the like refer to chemical moieties which mimic the side chain moieties of naturally physiologic amino acids.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"GLP-1 receptor agonist compounds" refer to compounds that elicit a biological activity of an exendin reference peptide (e.g., exendin-4) or a GLP-1(7-37) reference peptide when evaluated by art-known measures such as receptor binding studies or in vivo blood glucose assays as described by, e.g., Hargrove et al, 2007, *Regulatory Peptides,* 141:113-119, the disclosure of which is incorporated by reference herein. GLP-1 receptor agonist compounds include, for example, native exendins, exendin analogs, native GLP-1, GLP-1 analogs, GLP-1(7-37), and GLP-1(7-37) analogs.

The term "exendin" includes naturally occurring (or synthetic versions of naturally occurring) exendin peptides as described herein. Exendins include the amidated forms, the acid form, the pharmaceutically acceptable salt form, and any other physiologically active form of the molecule. In one embodiment, the term exendin can be used interchangeably with the term "exendin agonist." Absent express indication to the contrary, all peptides described herein are contemplated in the amidated and free acid forms.

"Exendin analog" refers to peptides, peptides containing peptide mimetics, amino acid substitutions, and/or other modifications, peptides containing the N-terminus conformationally constrained compounds described herein, and/or other chemical moieties, or other compounds which elicit a biological activity similar to that of an exendin reference peptide (e.g., exendin-4), when evaluated by art-known measures such as receptor binding assays or in vivo blood glucose assays as described, e.g., by Hargrove et al., 2007, *Regulatory Peptides* 141:113-119, the disclosure of which is incorporated by reference herein and for all purposes. Preferably, the exendin analogs will bind in such receptor binding assays with an affinity of less than 1 μM; an affinity of less than 5 nM; an affinity of less than 1 nM, or an affinity of less than 0.1 nM. In one embodiment, the term "exendin analog" refers to a peptide that has an amino acid sequence with 1, 2, 3, 4, 5, 6, 7, or 8 amino acid substitutions, insertions, deletions, or a combination of two or more thereof, when compared to the amino acid sequence of exendin-4. In one embodiment, the term exendin analog is an exendin-4 analog. In other embodiment, the term "exendin analog" refers to a peptide that has at least 85%, at least 88%, at least 90%, at least 93%, at least 95%, or at least 98% sequence identity to the amino acid sequence of exendin-4. Exendin analogs include the amidated forms, the acid form, the pharmaceutically acceptable salt form, and any other physiologically active form of the molecule. In one embodiment, the term exendin analog can be used interchangeably with the term "exendin agonist analog."

"GLP-1(7-37) analogs" refers to peptides, peptides containing peptide mimetics and/or other modifications, peptides containing the N-terminus conformationally constrained compounds described herein, and/or other chemical moieties, or other compounds which elicit a biological activity similar to that of GLP-1(7-37), when evaluated by art-known measures such as receptor binding assays or in vivo blood glucose assays as described, e.g., by Hargrove et al., 2007 (Id.) In one embodiment, the term "GLP-1(7-37) analog" refers to a peptide that has an amino acid sequence with 1, 2, 3, 4, 5, 6, 7, or 8 amino acid substitutions, insertions, deletions, or a combination of two or more thereof, when compared to the amino acid sequence of GLP-1(7-37). In one embodiment, the GLP-1(7-37) analog is GLP-1(7-36). GLP-1(7-37) analogs include the amidated forms, the acid form, the pharmaceutically acceptable salt form, and any other physiologically active form of the molecule.

The disclosure provides benzamide-containing peptide compounds having at least 50% amino acid sequence identity with Formula (I):

wherein the Xaa substituents are as defined herein and wherein one or more contiguous amino acid residues of Formula (I) are substituted with a 1-6 benzamide groups. The benzamide groups are designed to mimic one or more properties (e.g., shape, charge distribution, bulk and the like) of the side chain of a physiologic amino acid (e.g., Ala, Cys, Asp, Glu, Phe, Gly, His, Ile, Lys, Leu, Met, Asn, Pro, Gln, Arg, Ser, Thr, Val, Trp or Tyr) of Formula (I). The side chain surrogate moiety is attached to the phenyl ring forming the benzamide element. In one embodiment, 2, 3, 4, 5, 6, 7, 8, 9, 10, 11, or 12 contiguous amino acid residues of Formula (I) are substituted with the benzamide group $Y_1$ described herein. In one embodiment, 4, 5, 6, 7, 8, 9, or 10 contiguous amino acid residues of Formula (I) are substituted with the benzamide group $Y_1$ described herein. In one embodiment, 5, 6, 7, 8, or 9 contiguous amino acid residues of Formula (I) are substituted with the benzamide group $Y_1$ described herein. In one embodiment, the benzamide-containing peptide compounds have at least 75% sequence identity with Formula (I). In one embodiment, the benzamide-containing peptide compounds have at least 80% sequence identity with Formula (I). In one embodiment, the benzamide-containing peptide compounds have at least 85% sequence identity with Formula (I). In one embodiment, the benzamide-containing peptide compounds have at least 88% sequence identity with Formula (I). In one embodiment, the benzamide-containing peptide compounds have at least 92% sequence identity with Formula (I). In one embodiment, the benzamide-containing peptide compounds have at least 95% sequence identity with Formula (I).

In Formula (I), $Xaa_1$ is His, des-amino His, or

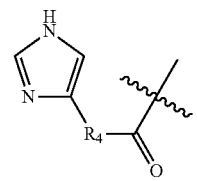

wherein $R_4$ is a bond, substituted or unsubstituted alkylenyl, or substituted or unsubstituted alkenylenyl. In one embodiment, $R_4$ is a bond. In one embodiment, $R_4$ is a $C_1$, $C_2$, $C_3$, or $C_4$ alkylenyl optionally substituted with alkyl, hydroxy or carboxy. In one embodiment, $R_4$ is methylene. In one embodiment, $R_4$ is ethylenyl substituted with one or more substituents $R_5$, wherein $R_5$ is independently alkyl, hydroxy or carboxy. In one embodiment, $R_4$ is unsubstituted alkenylenyl, preferably ethenylenyl. In one embodiment, $Xaa_1$ has the structure following:

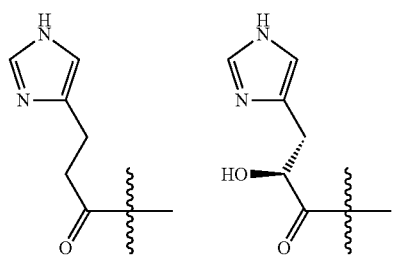

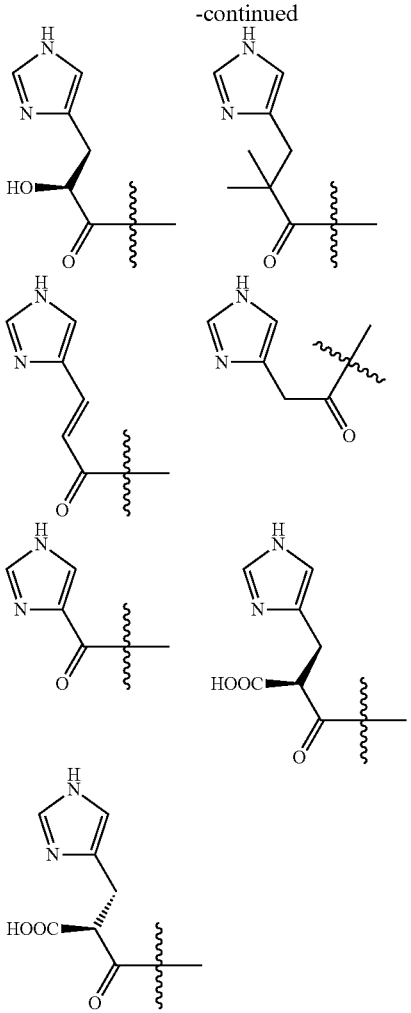

In one embodiment, Xaa$_1$ is His or des-amino His.

In Formula (I), Xaa$_2$ is Gly, Ala, D-Ala or Aib. In one embodiment, Xaa$_2$ is Gly, d-Ala or Ala. In one embodiment, Xaa$_2$ is Gly or Ala. In one embodiment, Xaa$_2$ is Gly.

In Formula (I), Xaa$_3$ is Gly, Ala, D-Ala, Aib, Glu, Pro, or a moiety selected from the group consisting of:

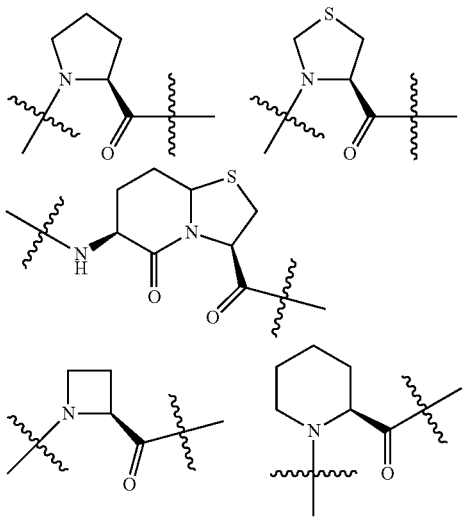

In one embodiment, Xaa$_3$ is Gly, Ala, Glu, or Pro. In one embodiment, Xaa$_3$ is Gly or Pro. In one embodiment, Xaa$_3$ is Gly. In one embodiment, Xaa$_3$ is Pro.

In Formula (I), Xaa$_{14}$ is Met or Leu. In one embodiment, Xaa$_{14}$ is Met. In one embodiment, Xaa$_{14}$ is Leu.

In Formula (I), Xaa$_{25}$ is Tip or Phe. In one embodiment, Xaa$_{25}$ is Tip. In one embodiment, Xaa$_{25}$ is Phe.

In Formula (I), Z is —OH; —NH$_2$; Gly Gly-OH; Gly Gly-NH$_2$; Gly Gly Pro Ser Ser Gly Ala Pro Pro Pro Ser-OH (SEQ ID NO: 5); or Gly Gly Pro Ser Ser Gly Ala Pro Pro Pro Ser-NH$_2$ (SEQ ID NO: 6). In one embodiment, Z is —OH; —NH$_2$; Gly Gly-OH; or Gly Gly-NH$_2$. In one embodiment, Z is —OH or —NH$_2$. In one embodiment, Z is —NH$_2$.

In Formula (I), Y$_1$ is:

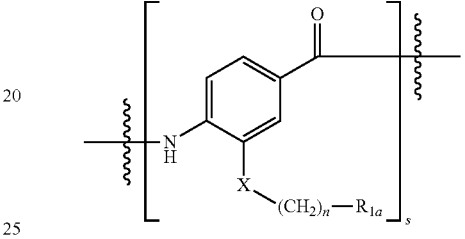

In the structure represented by Y$_1$, X is a bond, oxygen, sulfur, —NH—, —NR'—, substituted or unsubstituted alkylenyl, or substituted or unsubstituted alkenylenyl. In one embodiment, X is oxygen or a C$_1$ or C$_2$ alkenylenyl group. In one embodiment, X is oxygen.

In the structure represented by Y$_1$, R' is substituted or unsubstituted alkyl. In one embodiment, R' is a C1, C2, or C3 unsubstituted, straight or branched alkyl.

In the structure represented by Y$_1$, n is an integer from 0 to 6. In one embodiment, n is 1, 2, or 3. In one embodiment, n is 1 or 2.

In the structure represented by Y$_1$, R$_{1a}$ is hydrogen, halogen, hydroxy, thiol, carboxyl, substituted or unsubstituted carboxamido, carbamoyl, substituted or unsubstituted amino, substituted or unsubstituted imino, substituted or unsubstituted urea, nitro, nitroso, substituted or unsubstituted, straight or branched alkyl, substituted or unsubstituted alkenyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted alkyloxy, substituted or unsubstituted alkenyloxy, substituted or unsubstituted cycloalkyloxy, substituted or unsubstituted heteroalkyloxy, substituted or unsubstituted heterocycloalkyloxy, substituted or unsubstituted aryloxy, substituted or unsubstituted heteroaryloxy, substituted or unsubstituted alkylthio, substituted or unsubstituted alkenylthio, substituted or unsubstituted cycloalkylthio, substituted or unsubstituted heteroalkylthio, substituted or unsubstituted heterocycloalkylthio, substituted or unsubstituted arylthio, substituted or unsubstituted heteroarylthio, substituted or unsubstituted alkylsulfinyl, substituted or unsubstituted alkenylsulfinyl, substituted or unsubstituted cycloalkylsulfinyl, substituted or unsubstituted heteroalkylsulfinyl, substituted or unsubstituted heterocycloalkylsulfinyl, substituted or unsubstituted arylsulfinyl, substituted or unsubstituted heteroarylsulfinyl, substituted or unsubstituted alkylsulfonyl, substituted or unsubstituted alkenylsulfonyl, substituted or unsubstituted cycloalkylsulfonyl, substituted or unsubstituted heteroalkylsulfonyl, substituted or unsubstituted heterocycloalkylsulfonyl, substituted or unsubstituted arylsulfonyl, or substituted or unsubstituted heteroarylsulfonyl. In one embodiment, $R_{1a}$ is hydrogen, halogen, hydroxy, thiol, carboxyl, a substituted or unsubstituted, straight or branched $C_1$ $C_2$, $C_3$, $C_4$, $C_5$, or $C_6$ alkyl group; a substituted or unsubstituted cycloalkyl, a substituted or unsubstituted heteroalkyl, a substituted or unsubstituted heterocycloalkyl, a substituted or unsubstituted aryl, a substituted or unsubstituted heteroaryl. In one embodiment, $R_{1a}$ is an unsubstituted straight or branched $C_1$ $C_2$, $C_3$, or $C_4$ alkyl group, an unsubstituted aryl, or an unsubstituted heteroaryl. In one embodiment, $R_{1a}$ is an unsubstituted straight or branched $C_1$ $C_2$, or $C_3$ alkyl group, or an unsubstituted aryl. In one embodiment, $R_{1a}$ is unsubstituted.

In the structure represented by $Y_1$, S is an integer of 1, 2, 3, 4, 5, or 6. In one embodiment, S is an integer of 2, 3, or 4. In one embodiment, S is 3.

In some embodiments, each substituted group described above for the compounds of the present invention is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described above is substituted with at least one substituent group.

In other embodiments of the compounds described above, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_4$-$C_8$ cycloalkylene, and each substituted or unsubstituted heterocycloalkylene is a substituted or unsubstituted 4 to 8 membered heterocycloalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_5$-$C_7$ cycloalkylene, and each substituted or unsubstituted heterocycloalkylene is a substituted or unsubstituted 5 to 7 membered heterocycloalkylene.

In one embodiment, the benzamide-containing peptide compound of Formula (I) is more particularly represented by the following benzamide-containing peptide compound of Formula (II):

$Xaa_1$ $Xaa_2$ $Xaa_3$ Gly Thr Phe Thr Ser Asp $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$-$Y_1$—Z    (II) (SEQ ID NO: 7)

Wherein $Xaa_1$, $Xaa_2$, $Xaa_3$, $Xaa_{14}$, $Xaa_{25}$, $Y_1$ and Z have the same meaning as set forth for the peptide compound of Formula (I), and wherein $Xaa_{10}$ is Leu or absent (preferably Leu); $Xaa_{11}$ is Ser or absent (preferably Ser); $Xaa_{12}$ is Lys or absent (preferably Lys); $Xaa_{13}$ is Gln or absent (preferably Gln); $Xaa_{15}$ is Glu or absent (preferably Glu); $Xaa_{16}$ is Glu or Ala (preferably Glu); $Xaa_{17}$ is Glu or Ala (preferably Glu); $Xaa_{19}$ is Val or absent (preferably Val); $Xaa_{20}$ is Arg or absent (preferably Arg); and $Xaa_{21}$ is Leu or absent (preferably Leu).

The disclosure also provides benzamide-containing peptide compounds have at least 75% sequence identity with Formula (II). In one embodiment, the benzamide-containing peptide compounds have at least 80% sequence identity with Formula (II). In one embodiment, the benzamide-containing peptide compounds have at least 85% sequence identity with Formula (II). In one embodiment, the benzamide-containing peptide compounds have at least 88% sequence identity with Formula (II). In one embodiment, the benzamide-containing peptide compounds have at least 92% sequence identity with Formula (II). In one embodiment, the benzamide-containing peptide compounds have at least 95% sequence identity with Formula (II).

Representative compounds that fall within the scope of the peptide compound of Formula (II) include Compound Nos. 12, 13, 14, and 15.

In one embodiment, the benzamide-containing peptide compound of Formula (I) is more particularly represented by the following benzamide-containing peptide compound of Formula (III):

$Xaa_1$ $Xaa_2$ $Xaa_3$ Gly Thr $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala Val Arg

Leu Phe Ile Glu $Xaa_{25}$ Leu Lys Asn-Z    (III) (SEQ ID NO: 8)

Wherein $Xaa_1$, $Xaa_2$, $Xaa_3$, $Xaa_{25}$, and Z have the same meaning as set forth for the peptide compound of Formula (I). In the compound of Formula (III), $Xaa_6$-$Xaa_{14}$ are collectively taken together to be selected from the following: Phe Thr Ser $Y_1$; Phe $Y_1$ Gln Met; Phe Thr $Y_1$ Met; $Y_1$ Lys Gln Met; Phe $Y_1$ Gln Leu; Phe Thr $Y_1$ Leu; $Y_1$ Lys Gln Leu; $Y_1$ Ser Lys Gln Met (SEQ ID NO: 9); Phe $Y_1$ Lys Gln Met (SEQ ID NO: 10); Phe Thr $Y_1$ Gln Met (SEQ ID NO: 11); Phe Thr Ser $Y_1$ Met (SEQ ID NO: 12); Phe Thr Ser Asp $Y_1$ (SEQ ID NO: 13); $Y_1$ Ser Lys Gln Leu (SEQ ID NO: 14); Phe $Y_1$ Lys Gln Leu (SEQ ID NO: 15); Phe Thr $Y_1$ Gln Leu (SEQ ID NO: 16); Phe Thr Ser $Y_1$ Leu (SEQ ID NO: 17); Phe Thr Ser Asp Leu $Y_1$ (SEQ ID NO: 18); Phe Thr Ser Asp $Y_1$ Met (SEQ ID NO: 19); Phe Thr Ser $Y_1$ Gln Met (SEQ ID NO: 20); Phe Thr $Y_1$ Lys Gln Met (SEQ ID NO: 21); Phe $Y_1$ Ser Lys Gln Met (SEQ ID NO: 22); $Y_1$ Leu Ser Lys Gln Met (SEQ ID NO: 23); Phe Thr Ser Asp $Y_1$ Leu (SEQ ID NO: 24); Phe Thr Ser $Y_1$ Gln Leu (SEQ ID NO: 25); Phe Thr $Y_1$ Lys Gln Leu (SEQ ID NO: 26); Phe $Y_1$ Ser Lys Gln Leu (SEQ ID NO: 27); and $Y_1$ Leu Ser Lys Gln Leu (SEQ ID NO: 28). The skilled artisan will appreciate that in order for $Xaa_6$-$Xaa_{14}$ to be collectively taken together to represent these amino acid residues in conjunction with the chemical moiety $Y_1$, some of the amino acid residues represented by $Xaa_6$-$Xaa_{14}$ will be absent from the compound. In other words, each of $Xaa_6$ through $Xaa_{14}$ will not correspond to an amino acid residue or $Y_1$ and will thus be absent from the compound.

For the compound of Formula (III), $Y_1$ has the same meaning as defined for the compound of Formula (I); $Xaa_{15}$ is Glu or absent (preferably Glu); $Xaa_{16}$ is Glu or Ala (preferably Glu); and $Xaa_{17}$ is Glu or Ala (preferably Glu).

The disclosure also provides benzamide-containing peptide compounds have at least 75% sequence identity with Formula (III). In one embodiment, the benzamide-containing peptide compounds have at least 80% sequence identity with Formula (III). In one embodiment, the benzamide-containing peptide compounds have at least 85% sequence identity with Formula (III). In one embodiment, the benzamide-containing peptide compounds have at least 88% sequence identity with Formula (III). In one embodiment, the benzamide-containing peptide compounds have at least 92% sequence identity with Formula (III). In one embodiment, the benzamide-containing peptide compounds have at least 95% sequence identity with Formula (III).

Representative compounds that fall within the scope of the peptide compound of Formula (III) include Compound Nos. 16, 17, and 18.

Exemplary compounds described herein are set forth in Table 1 following. As customary in the art and as used herein, a lower case one-letter amino acid code (e.g., "a") indicates a D-amino acid (such that "a" in a sequence listing refers to D-Ala). The symbols "—NH—," "—NH$_2$" and the like refer to amine nitrogen with attached hydrogen(s), and the symbol "N" as part of a peptide, and not part of a bridgehead, refers to Asn. "Bridgehead" as used herein refers in the customary sense to the point of attachment of a bridge (e.g., an alkenylenyl bridge) in a molecule (e.g., a peptide). The term "H" when part of a peptide refers to His, whereas "H" when used in the terms "—NH—," "—NH$_2$" and the like refers to hydrogen.

TABLE 1

| Cmpd No. | Compound |
|---|---|
| 2 (SEQ ID NO: 29) |  |
| 13 (SEQ ID NO: 30) | 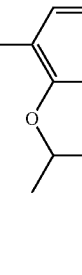 |
| 14 (SEQ ID NO: 31) | 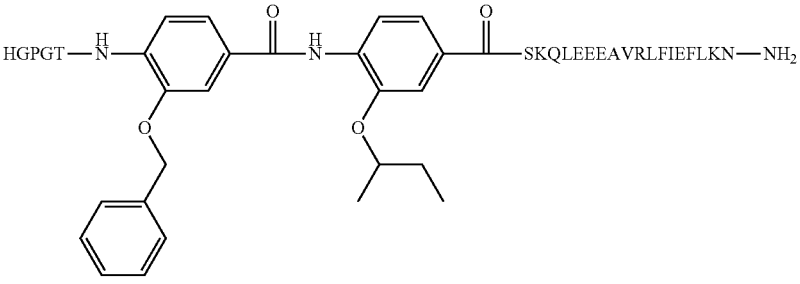 |
| 15 (SEQ ID NO: 32) | 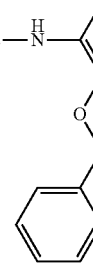 |

TABLE 1-continued

| Cmpd No. | Compound |
|---|---|
| 16 (SEQ ID NO: 33) | HaPGTFTSDAAAVRL—[structure with two benzyloxy-benzamide linkers ending in NH₂] |
| 17 (SEQ ID NO: 34) | HaPGTFTSDLSKQLEEEA—[structure with isopropoxy linker and two benzyloxy-benzamide linkers ending in NH₂] |
| 18 (SEQ ID NO: 35) | HaPGTFTSDAAARL—[structure with two benzyloxy-benzamide linkers ending in NH₂] |

In another aspect, there is provided a constrained alkene peptide compounds comprising an amino acid sequence having at least 50% sequence identity with the structure of Formula (IV):

Xaa₁-Xaa₂-Xaa₃-GTFTSDLSKQ-Xaa₁₄-EEEAVR-LFIE-Xaa₂₅-LKN-Z    (IV) (SEQ ID NO: 2)

Wherein Xaa₁, Xaa₂, Xaa₃, Xaa₁₄, Xaa₂₅, and Z have the same definition as that for Formula (I) and wherein at least one pair of amino acid residues is linked by an alkenylenyl bridge or an alkylenyl bridge. In one embodiment, at least one pair of amino acid residues is linked by an alkenylenyl bridge. In one embodiment, the amino acid residues that are linked by the alkenylenyl bridge are separated by 2, 3, or 4 amino acid residues; preferably by 3 amino acid residues. The terms "constrained GLP-1 receptor agonist," "constrained peptide compound," "constrained compound," "constrained alkene compound" and the like refer to peptide compounds wherein at least one pair of residues has been substituted such that an alkenylenyl bridge or an alkylenyl bridge connects the pair. The disclosure also provides constrained alkene peptide compounds have at least 75% sequence identity with Formula (IV). In one embodiment, the constrained alkene peptide compounds have at least 80% sequence identity with Formula (IV). In one embodiment, the constrained alkene peptide compounds have at least 85% sequence identity with Formula (IV). In one embodiment, the constrained alkene peptide compounds have at least 88% sequence identity with Formula (IV). In one embodiment, the constrained constrained alkene peptide compounds have at least 92% sequence identity with Formula (IV). In one embodiment, the constrained alkene peptide compounds have at least 95% sequence identity with Formula (IV).

In Formula (IV), the alkenylenyl bridge is represented by the following:

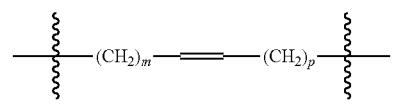

wherein m and p are each independently 1, 2, 3, 4, 5, or 6; preferably 1, 2, or 3; more preferably 1 or 2. In certain embodiments, a single alkenylenyl bridge is present. In certain embodiments, a plurality, e.g., 2, 3 or even 4, of alkenylenyl bridges are present.

In certain embodiments, the alkenylenyl bridge connects the backbone $C_\alpha$ atoms of the amino acid pair joined by the alkenylenyl bridge. In certain embodiments, the alkenylenyl bridge connects a backbone $N_\alpha$ of one residue with the backbone $C_\alpha$ carbon of the other amino acid. In certain embodiments, the alkenylenyl bridge connects a backbone $N_\alpha$ of one residue with the backbone $N_\alpha$ of the other amino acid. In certain embodiments, the alkenylenyl bridge is reduced to form an alkylenyl bridge, as known in the art.

In one embodiment, the constrained alkene peptide compounds of Formula (IV) is more particularly represented by the following constrained alkene peptide compounds of Formula (V):

Xaa$_1$ Xaa$_2$ Xaa$_3$ Gly Thr Phe Thr Ser Asp Leu

Ser Lys Gln Xaa$_{14}$ Glu Glu Glu Ala Val Arg

Leu Phe Ile Y$_2$—Z                    (V) (SEQ ID NO: 36);

Wherein Xaa$_1$, Xaa$_2$, Xaa$_3$, Xaa$_{14}$, and Z have the same meanings as set forth in Formula (I) and wherein Y$_2$ is:

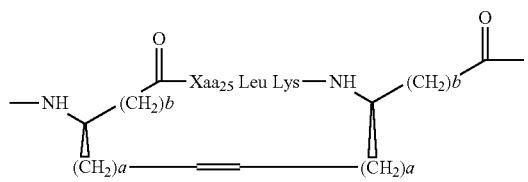

Wherein Xaa$_{25}$ is Phe or Trp; a is 1, 2, or 3; b is 0, 1, or 2; and is ▲, ≡ or |. In one embodiment, Xaa$_{25}$ is Phe. In one embodiment, Xaa$_{25}$ is Trp. In one embodiment, a is 1 or 2. In one embodiment, a is 1. In one embodiment, b is 0 or 1. In one embodiment, b is 1. In one embodiment, b is 0. When b is 0, then (CH$_2$)b is a single bond in which the carbon atom to the left of (CH$_2$)b is linked to the carbon atom to the right of (CH$_2$)b by a single bond. For the sake of clarity, the only amino acids identified in Y$_2$ are Xaa$_{25}$, Leu, and Lys; all other letters refer to nitrogen, oxygen, and carbon.

The disclosure also provides constrained alkene peptide compounds have at least 75% sequence identity with Formula (V). In one embodiment, the constrained alkene peptide compounds have at least 80% sequence identity with Formula (V). In one embodiment, the constrained alkene peptide compounds have at least 85% sequence identity with Formula (V). In one embodiment, the constrained alkene peptide compounds have at least 88% sequence identity with Formula (V). In one embodiment, the constrained alkene peptide compounds have at least 92% sequence identity with Formula (V). In one embodiment, the constrained alkene peptide compounds have at least 95% sequence identity with Formula (V).

Representative compounds that fall within the scope of the constrained alkene peptide compounds of Formula (V) include Compound Nos. 22, 23, 24, 25, 26, and 27.

In one embodiment, the constrained alkene peptide compounds of Formula (IV) is more particularly represented by the following constrained alkene peptide compounds of Formula (VI):

Xaa$_1$ Xaa$_2$ Xaa$_3$ Gly Thr Phe Thr Ser Asp Leu

Ser Lys Gln Xaa$_{14}$ Glu Glu Glu Ala Val Arg

Leu Phe Ile Y$_3$—Z                    (VI) (SEQ ID NO: 37);

Wherein Xaa$_1$, Xaa$_2$, Xaa$_3$, Xaa$_{14}$, and Z have the same meanings as set forth in Formula (I), and wherein Y$_3$ is:

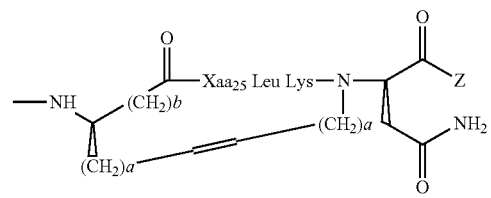

Wherein Xaa$_{25}$ is Phe or Trp; a is 1, 2, or 3; b is 0, 1, or 2; and is ▲, ≡ or |. In one embodiment, Xaa$_{25}$ is Phe. In one embodiment, Xaa$_{25}$ is Trp. In one embodiment, a is 1 or 2. In one embodiment, b is 0 or 1. In one embodiment, b is 0. When b is 0, then (CH$_2$)b is a single bond in which the carbon atom to the left of (CH$_2$)b is linked to the carbon atom to the right of (CH$_2$)b by a single bond. For the sake of clarity, the only amino acids identified in Y$_3$ are Xaa$_{25}$, Leu, and Lys; all other letters refer to nitrogen, oxygen, and carbon; except for Z which has the same definition as that set forth for Formula (I).

The disclosure also provides constrained alkene peptide compounds have at least 75% sequence identity with Formula (VI). In one embodiment, the constrained alkene peptide compounds have at least 80% sequence identity with Formula (VI). In one embodiment, the constrained alkene peptide compounds have at least 85% sequence identity with Formula (VI). In one embodiment, the constrained alkene peptide compounds have at least 88% sequence identity with Formula (VI). In one embodiment, the constrained alkene peptide compounds have at least 92% sequence identity with Formula (VI). In one embodiment, the constrained alkene peptide compounds have at least 95% sequence identity with Formula (VI).

Representative compounds that fall within the scope of the constrained alkene peptide compounds of Formula (VI) include Compound Nos. 34, 35, and 36.

Exemplary peptide compounds of Formula (IV), (V), and (VI) described herein are provided in Table 2 following. It is understood that the term "N" when representing a bridgehead as described herein refers to nitrogen. It is further understood that the symbol "NH$_2$—H—" refers to N-terminal His having an N-terminal amide functionality.

TABLE 2

| Cmpd No. | Compound |
|---|---|
| 22 (SEQ ID NO: 38) | NH$_2$—H—N(H)—C(O)—PGTFTSDLSKQLEEEAVRLFI—N(H)—C(O)—F—L—K—N(H)—C(O)—NH$_2$ |

TABLE 2-continued

| Cmpd No. | Compound |
|---|---|
| 23 (SEQ ID NO: 39) | NH₂—H—N(H)—[C(=O)]—PGTFTSDLSKQLEEEAVRLFI—N(H)—[C(=O)]—F—L—K—N(H)—[C(=O)]—NH₂ (with crosslinking alkene) |
| 24 (SEQ ID NO: 40) | NH₂—H—N(H)—[C(=O)]—PGTFTSDLSKQLEEEAVRLFI—N(H)—[C(=O)]—F—L—K—N(H)—[C(=O)]—NH₂ (with crosslinking alkene) |
| 25 (SEQ ID NO: 41) | NH₂—H—N(H)—[C(=O)]—PGTFTSDLSKQLEEEAVRLFI—N(H)—[C(=O)]—F—L—K—N(H)—[C(=O)]—NH₂ (with crosslinking alkene) |
| 26 (SEQ ID NO: 42) | NH₂—H—N(H)—[C(=O)]—PGTFTSDLSKQLEEEAVRLFI—N(H)—[C(=O)]—F—L—K—N(H)—CH(CH₂C(=O)NH₂) with crosslinking alkene |
| 27 (SEQ ID NO: 43) | NH₂—H—N(H)—[C(=O)]—PGTFTSDLSKQLEEEAVRLFI—N(H)—[C(=O)]—F—L—K—N(H)—CH(CH₂C(=O)NH₂) with crosslinking alkene |
| 34 (SEQ ID NO: 44) | NH₂—H—N(H)—[C(=O)]—PGTFTSDLSKQLEEEAVRLFI—N(H)—[C(=O)]—F—L—K—N—CH(C(=O)NH₂)(CH₂C(=O)NH₂) with crosslinking alkene |
| 35 (SEQ ID NO: 45) | NH₂—H—N(H)—[C(=O)]—PGTFTSDLSKQLEEEAVRLFI—N(H)—[C(=O)]—F—L—K—N—CH(C(=O)NH₂)(CH₂C(=O)NH₂) with crosslinking alkene |
| 36 (SEQ ID NO: 46) | NH₂—H—N(H)—[C(=O)]—PGTFTSDLSKQLEEEAVRLFI—N(H)—[C(=O)]—F—L—K—N—CH(C(=O)NH₂)(CH₂C(=O)NH₂) with crosslinking alkene |

In certain embodiments, the peptide compounds described herein are linked to one, two, or three polyethylene glycol polymers. In one embodiment, the compounds are linked to one polyethylene glycol. The polyethylene glycol can have a molecular weight from about 200 daltons to about 80,000 daltons; from about 5,000 from about 10,000 daltons to about 60,000 daltons; from about 10,000 daltons to about 50,000 daltons; or from about 15,000 daltons to about 40,000 daltons. The polyethylene glycol may be linear or branched.

In certain embodiments, compounds are linked to one or two polyethylene glycols, where the polyethylene glycol is further linked to a lipophilic moiety. In one embodiment, the polyethylene glycol may have a molecular weight from about 200 to about 7,000 daltons or from about 500 to about 5,000 daltons. The lipophilic moiety may be an alkyl group (e.g., C1-20 alkyl group; C1-10 alkyl group; C1-6 alkyl group; C1-4 alkyl group), a fatty acid (e.g., C4-28 fatty acid chain; C8-24 fatty acid chain; C10-20 fatty acid chain), cholesteryl, adamantyl, and the like. The alkyl group may be linear or branched, preferably linear. In one embodiment, the fatty acid is an acetylated fatty acid or an esterified fatty acid. The -(polyethylene glycol)-(lipophilic moiety) may be linked to the compound at a C-terminal amino acid residue, an N-terminal amino acid residue, an internal amino acid residue (e.g., an internal Lys amino acid residue), or a combination thereof (e.g., the compound is linked at the N-terminal and C-terminal amino acid residues).

In certain embodiments, the compounds are linked to a polyamino acid. Exemplary polyamino acids include poly-lysine, poly-aspartic acid, poly-serine, poly-glutamic acid, and the like. The polyamino acid may be in the D or L form, preferably the L form. The polyamino acids may comprise from 1 to 12 amino acid residues; from 2 to 10 amino acid residues; or from 2 to 6 amino acid residues.

In certain embodiments, compounds are linked to a fatty acid. The fatty acid may be a $C_4$-$C_{28}$ fatty acid chain, a $C_8$-$C_{24}$ fatty acid chain, or a $C_{10}$-$C_{20}$ fatty acid chain. In one embodiment, the fatty acid is an acetylated fatty acid. In one embodiment, the fatty acid is an esterified fatty acid.

In certain embodiments, the compounds are linked to albumin. The albumin may be a recombinant albumin, serum albumin, or recombinant serum albumin. In another embodiment, the compounds are linked to an albumin-fatty acid (i.e., an albumin linked to a fatty acid).

In one embodiment, the compounds are linked to an immunoglobulin or an immunoglobulin Fc region. The immunoglobulin may be IgG, IgE, IgA, IgD, or IgM. In one embodiment, the compounds are linked to an IgG Fc region or an IgM Fc region. The immunoglobulin Fc region is (i) the heavy chain constant region 2(CH2) of an immunoglobulin; (ii) the heavy chain constant region 3(CH3) of an immunoglobulin; or (iii) both the heavy chain constant regions 2(CH2) and 3(CH3) of an immunoglobulin. The immunoglobulin Fc region may further comprise the hinge region at the heavy chain constant region. Other embodiments for the immunoglobulin Fc region that can be linked to exendin analog peptides are described in WO 2008/082274, the disclosure of which is incorporated by reference herein.

When the compounds described herein are covalently linked to one or more polymers, such as those described herein, any linking group known in the art can be used. The linking group may comprise any chemical group(s) suitable for linking the peptide to the polymer. Alternatively, compounds can be directly attached to the polymer without any linking group. Exemplary linking groups include amino acids, maleimido groups, dicarboxylic acid groups, succinimide groups, or a combination of two or more thereof. Methods for linking peptides to one or more polymers are known in the art and described, for example, in U.S. Pat. No. 6,329,336; U.S. Pat. No. 6,423,685; U.S. Pat. No. 6,924,264; WO 2005/077072, WO 2007/022123, WO 2007/053946; WO 2008/058461; and WO 2008/082274, the disclosures of which are incorporated by reference herein.

General methods of peptide synthesis. Certain peptide elements of the compounds described herein may be prepared using biological, chemical, and/or recombinant DNA techniques that are known in the art. Exemplary peptide synthetic methods are described herein and in U.S. Pat. No. 6,872,700; WO 2007/139941; WO 2007/140284; WO 2008/082274; WO 2009/011544; and US Publication No. 2007/0238669, the disclosures of which are incorporated herein by reference in their entireties and for all purposes. Other methods for preparing the compounds are set forth herein and/or known in the art.

For example, the peptide components of the compounds described herein may be prepared using standard solid-phase peptide synthesis techniques, such as an automated or semi-automated peptide synthesizer. Typically, using such techniques, an alpha-N-carbamoyl protected amino acid and an amino acid attached to the growing peptide chain on a resin are coupled at room temperature in an inert solvent (e.g., dimethylformamide, N-methyl pyrrolidinone, methylene chloride, and the like) in the presence of coupling agents (e.g., dicyclohexylcarbodiimide, 1-hydroxybenzo-triazole, and the like) in the presence of a base (e.g., diisopropylethylamine, and the like). The alpha-N-carbamoyl protecting group is removed from the resulting peptide-resin using a reagent (e.g., trifluoroacetic acid, piperidine, and the like) and the coupling reaction repeated with the next desired N-protected amino acid to be added to the peptide chain. Suitable N-protecting groups are well known in the art, such as t-butyloxycarbonyl (tBoc) fluorenylmethoxycarbonyl (Fmoc), and the like. The solvents, amino acid derivatives and 4-methylbenzhydryl-amine resin used in the peptide synthesizer may be purchased from a variety of commercial sources, including for example Applied Biosystems Inc. (Foster City, Calif.).

For chemical synthesis solid phase peptide synthesis can be used for the peptide conjugates, since in general solid phase synthesis is a straightforward approach with excellent scalability to commercial scale, and is generally compatible with relatively long peptide conjugates. Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (See Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (e.g., Introduction to Cleavage Techniques, Applied Biosystems, Inc., 1990, pp. 6-12). Peptides may also be assembled using an Advanced Chem Tech Synthesizer (Model MPS 350, Louisville, Ky.).

The compounds described herein may also be prepared using recombinant DNA techniques using methods known in the art, such as Sambrook et al., 1989, *MOLECULAR CLONING: A LABORATORY MANUAL*, 2d Ed., Cold Spring Harbor. Non-peptide compounds may be prepared by art-known methods. For example, phosphate-containing amino acids and peptides containing such amino acids may be prepared using methods known in the art, such as described in Bartlett et al., 1986, *Biorg. Chem.*, 14:356-377.

Purification. Peptides may be purified by RP-HPLC (preparative and analytical) using e.g., a Waters Delta Prep 3000 system. A $C_4$, $C_8$ or $C_{18}$ preparative column (10μ, 2.2×25 cm; Vydac, Hesperia, Calif.) may be used to isolate peptides, and purity may be determined using a $C_4$, $C_8$ or $C_{18}$ analytical column (5μ, 0.46×25 cm; Vydac). Solvents (A=0.1% TFA/water and B=0.1% TFA/CH3CN) may be delivered to the analytical column at a flow rate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods. See, e.g., Cohen et al., 1989, *THE PICO TAG METHOD: A MANUAL OF ADVANCED TECHNIQUES FOR AMINO ACID ANALYSIS*, pp. 11-52, Millipore Corporation, Milford, Mass.). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer.

Reagents for solid-phase synthesis. Reagents (i.e., synthetic building blocks) having a side chain surrogate moiety, a free carboxylic acid and a nitro moiety useful for the solid-phase synthetic methods described herein are available by a variety of synthetic methods known in the art and/or described herein.

For example, as shown in Scheme 1, methyl 3-hydroxy-4-nitrobenzoate can react with an alcohol to provide a reagent useful for synthesis of the compounds described herein. By varying the substituent R in the alcohol in the reaction of Scheme 1, side chain surrogate moieties can be introduced into reagents. Exemplary syntheses are provided in the Examples.

Scheme 1

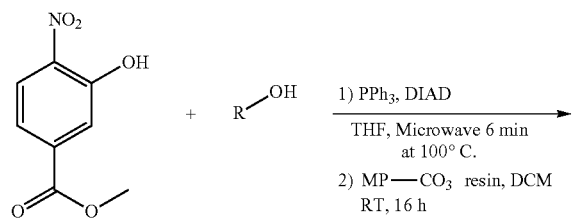

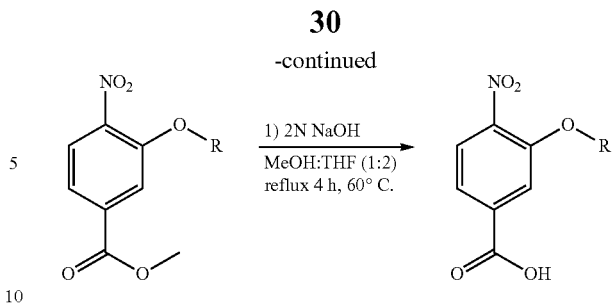

Synthesis of benzamide-containing peptide compounds. Solid-phase synthesis of benzamide-containing compounds is conveniently conducted on a resin (e.g., Rink amide resin). With reference to the following Scheme 2, reaction of the free amine of a nascent resin-bound peptide S1 with the carboxyl group of a suitable substituted nitrophenyl benzoate S2 results in the covalent introduction of a terminal benzamidyl moiety in resin-bound peptide S3.

Scheme 2

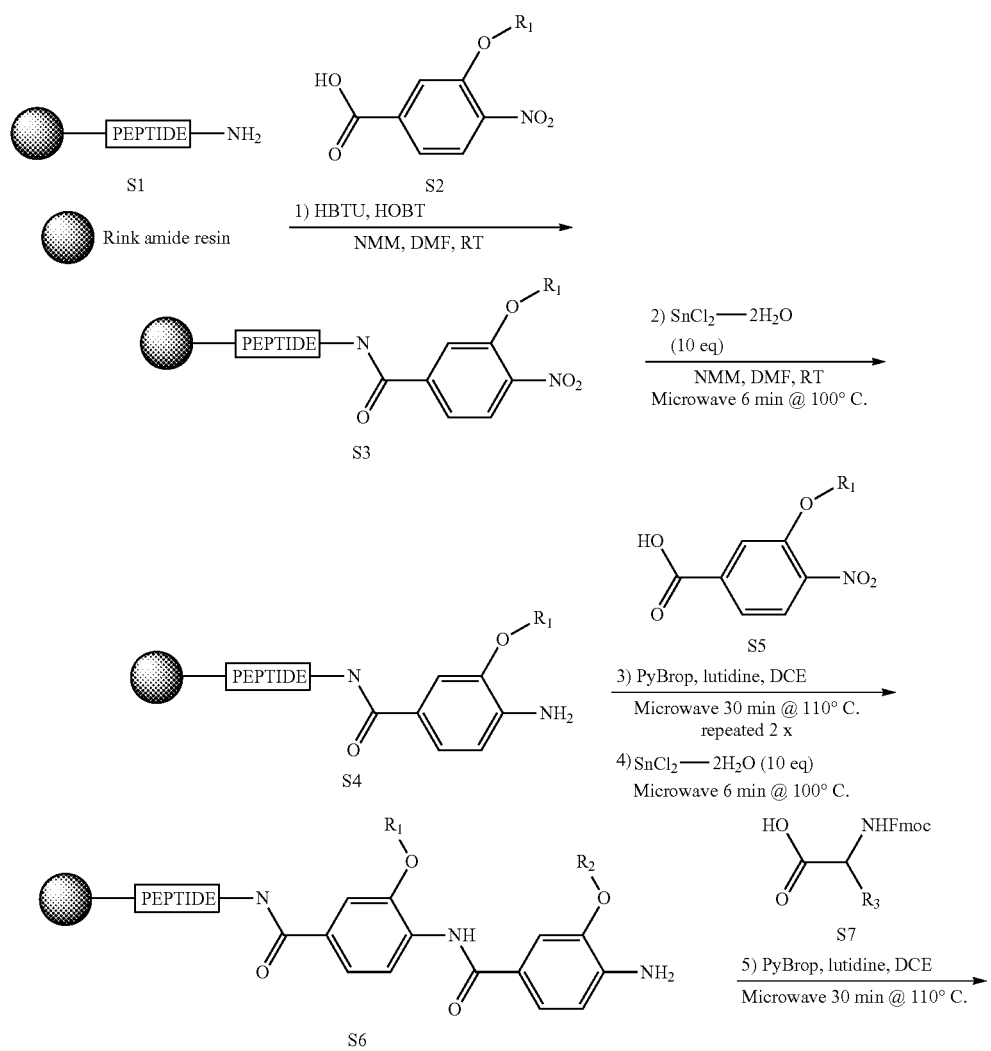

-continued

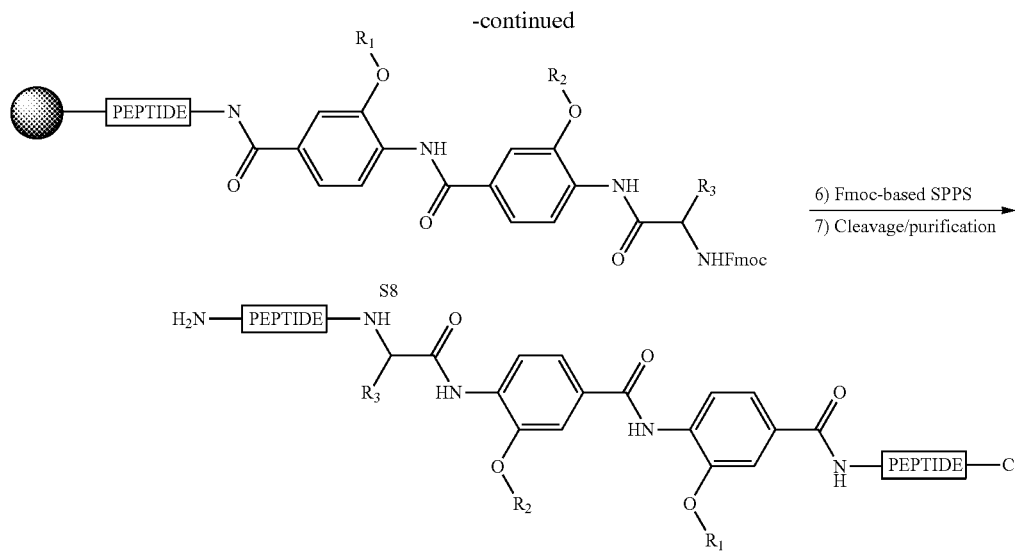

Surprisingly, it has been discovered that the nitro group of S3 can be easily reduced to the level of an amine, thereby forming a free amine for subsequent solid-phase reaction.

For example, in Scheme 2 an additional suitable substituted nitrophenyl benzoate is introduced, thereby forming a bis-benzamidyl compound. The terms "polybenzamide," "polybenzamidyl" and the like refer, in the customary sense, to a plurality of substituted phenyl moieties attached via amide linkage. The terms "bis-benzamide," "tris-benzamide" and the like refer, in the customary sense, to a specific number of phenyl moieties thus bonded. After introduction of one or more benzamide (polybenzamide) chemical features into a compound described herein, an N-terminal peptide sequence can be introduced prior to cleavage and purification.

Synthesis of benzamide-containing compounds. In a first aspect, there is provided a method for solid-phase synthesis of a substituted benzamide-containing peptide compound. The method includes the step of reacting a resin-bound reagent having a free amine with a substituted phenyl having a side chain surrogate moiety, a free carboxylic acid and a nitro moiety thereby forming a resin-bound substituted benzamidyl. The nitro moiety is reduced to form a free amine thereby forming a resin-bound substituted benzamidyl having a free amine. The terms "benzamide-containing compound," "benzamide-containing peptide" and the like refer to compounds described herein having a peptide component covalently bonded to a substituted phenyl via an amide bond. Two or more benzamides can be contiguous and linked by an amide bond, and this combination can in turn be linked to one or more peptide elements via amide bond(s). For example, if the benzamide (polybenzamide) is linked to the N-terminal or C-terminal residue of the peptide, then a single amide bond links the peptide element and the benzamide (polybenzamide). Alternatively, if the benzamide (polybenzamide) replaces one or more contiguous internal (i.e., neither N-terminal nor C-terminal) residues of the peptide element, then the benzamide (polybenzamide) attaches in turn to both the N-terminal and C-terminal amino acid residues of the peptide via amide bonds.

In certain embodiments, the previous steps are repeated to add one or more additional substituted phenyl moieties to the resin-bound substituted benzamidyl thereby forming an extended resin-bound substituted benzamidyl having a free amine.

In certain embodiments, the free amine of the benzamidyl moiety, either alone or as part of an extended resin-bound substituted benzamidyl, is reacted with additional amino acids thereby forming a substituted benzamide-containing compound.

In certain embodiments, the resin-bound reagent is a primary (i.e., "free") amine moiety bound to said resin. Accordingly, in this case the benzamide is conjugated to the C-terminal of the resulting benzamide-containing peptide.

In one embodiment, a polybenzamide reagent is reacted with the resin-bound reagent having a free amine. The polybenzamide reagent has a carboxylic group suitable to react with a resin-bound reagent having a free amine and a nitro group. The polybenzamide reagent is formed from phenyl groups linked via amide bonds, each phenyl having a side-chain surrogate moiety. After addition of the polybenzamide reagent to the resin, synthesis may proceed as described above.

Further to any of the synthesis methods described herein, it is understood that cleavage from a resin and subsequent purification is employed to afford compounds described herein.

The peptide compounds described herein and pharmaceutical compositions comprising the peptide compounds are useful for treating diabetes. The diabetes can be Type 1 diabetes, Type 2 diabetes, or gestational diabetes. In one embodiment, the diabetes is Type 2 diabetes. The methods for treating diabetes include administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein to treat diabetes in the patient. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein.

The compounds described herein and pharmaceutical compositions comprising the compounds are useful for treating pre-diabetes. The methods for treating diabetes include administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein to treat pre-diabetes in the patient. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein.

The compounds described herein and pharmaceutical compositions comprising the compounds are useful for treating insulin resistance and stimulating insulin release. The methods for treating insulin resistance include administering to a patient in need thereof a therapeutically effective amount of one or more of the benzamide-containing or constrained alkene compounds described herein to treat insulin resistance in the patient. The methods for stimulating insulin release include administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to stimulate insulin release in the patient. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein.

The compounds described herein and pharmaceutical compositions comprising the compounds are useful for treating postprandial hyperglycemia. The methods for treating postprandial hyperglycemia include administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to treat postprandial hyperglycemia in the patient. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein.

The compounds described herein and pharmaceutical compositions comprising the compounds are useful for lowering blood glucose levels and lowering HbA1c levels. The methods for lowering blood glucose levels include administering to a patient in need thereof a therapeutically effective amount of one or more of the benzamide-containing or constrained alkene compounds described herein to lower blood glucose levels in the patient. In one embodiment, the blood glucose levels can be fasting blood glucose levels. The methods for lowering HbA1c levels include administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to lower HbA1c levels in the patient. HbA1c levels are generally a long-term measure of a patient's blood glucose levels. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein.

The compounds described herein and pharmaceutical compositions comprising the compounds are useful for reducing gastric motility and delaying gastric emptying. The methods for reducing gastric motility include administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to reduce gastric motility in the patient. The methods for delaying gastric emptying include administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to delay gastric emptying in the patient. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein.

The compounds described herein and pharmaceutical compositions comprising the compounds are useful for reducing food intake, reducing appetite, and increasing satiety. The methods for reducing food intake include administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to reduce food intake in the patient. The methods for reducing appetite or increasing satiety include administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to reduce appetite in the patient. The patient may be of any weight, and can be overweight or obese. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein.

The compounds described herein and pharmaceutical compositions comprising the compounds are useful for reducing body weight. The methods for reducing body weight include administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to reduce body weight in the patient. The patient may be of any weight, and can be overweight or obese. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein.

The compounds described herein and pharmaceutical compositions comprising the compounds are useful for treating overweight and obesity. The methods for treating overweight provide administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein to treat overweight in the patient. The methods for treating obesity provide administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to treat obesity in the patient. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein.

"Obesity" and "overweight" refer to patients having a weight greater than normally expected, and may be determined by, e.g., physical appearance, body mass index (BMI) as known in the art, waist-to-hip circumference ratios, skinfold thickness, waist circumference, and the like. The Centers for Disease Control and Prevention (CDC) define overweight as an adult human having a BMI of 25 to 29.9; and define obese as an adult human having a BMI of 30 or higher. Additional metrics for the determination of obesity exist. For example, the CDC states that a person with a waist-to-hip ratio greater than 1.0 is overweight.

The compounds described herein and pharmaceutical compositions comprising the compounds are useful for treating cardiovascular disease. The methods for treating cardiovascular disease provide administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein to treat cardiovascular disease in the patient. The methods for treating cardiovascular disease provide administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to treat cardiovascular disease in the patient. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein. Cardiovascular disease includes heart disease, congestive heart failure, hypertension, peripheral vascular disease, angina, atherosclerosis, myocardial infarction, hypertriglyceridemia, and hypercholesterolemia.

The compounds described herein and pharmaceutical compositions comprising the compounds are useful for treating neurodegenerative diseases. The methods for treating neurodegenerative diseases provide administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein to treat neurodegenerative diseases in the patient. The methods for treating neurodegenerative diseases provide administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to treat cardiovascular disease in the patient. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein. Neurodegenerative diseases include Alzheimer's disease, Parkinson's disease, Huntington's disease, Pick's disease, and the like.

The compounds described herein and pharmaceutical compositions comprising the compounds are useful for treating obstructive sleep apnea. The methods for treating obstructive sleep apnea provide administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein to treat obstructive sleep apnea in the patient. The methods for treating obstructive sleep apnea provide administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to treat obstructive sleep apnea in the patient. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein.

The compounds described herein and pharmaceutical compositions comprising the compounds are useful for treating short bowel syndrome. The methods for treating short bowel syndrome provide administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formulat (IV), (V) or (VI)) described herein to treat short bowel syndrome in the patient. The methods for treating short bowel syndrome provide administering to a patient in need thereof a therapeutically effective amount of one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein to treat short bowel syndrome in the patient. In one embodiment, the methods provide administering a pharmaceutical composition comprising one or more of the benzamide-containing peptide compounds (e.g., a peptide compound of Formula (I), (II) or (III)) or one or more of the constrained alkene peptide compounds (e.g., a peptide compound of Formula (IV), (V) or (VI)) described herein.

The compounds described herein may be tested in a variety of receptor binding assays using methodologies generally known to those skilled in the art. Such assays include those described herein.

GLP-1 receptor binding assay. GLP-1 receptor binding activity and affinity may be measured using a binding displacement assay in which the receptor source is RINm5F cell membranes, and the ligand is [$^{125}$I]GLP-1. Homogenized RINm5F cell membranes can be incubated in 20 mM HEPES buffer with 40,000 cpm e25I]GLP-1 tracer, and varying concentrations of test compound for 2 hours at 23° C. with constant mixing. Reaction mixtures can be filtered through glass filter pads presoaked with 0.3% PE1 solution and rinsed with ice-cold phosphate buffered saline. Bound counts can be determined using a. scintillation counter. Binding affinities can be calculated using GraphPad Prism software (GraphPad Software, Inc., San Diego, Calif.).

GLP-1 adenylate cyclase assay (Functional Assay). The GLP-1 receptor mediated adenylate cyclase activation can be measured using, for example, an HTRF (Homogeneous Time-Resolved Fluorescence) cell-based cAMP assay kit (CisBio) as known in the art.

Glucose lowering assay. Suitable test animals (e.g., NIH/Swiss mice) can be fasted (e.g., 2-hr) prior to the assay. Pre-treatment glucose blood concentration can be determined. Compound or vehicle can be injected at zero time, and samples can be withdrawn at fixed intervals (e.g., 30, 60, 120, 180 and 240 min) for blood glucose determination. A suitable blood glucose measurement device is the One Touch® Ultra® (LifeScan, Inc., Milpitas, Calif.). Results can be presented as the integrated area under the curve ("AUC"). For example, "$AUC_{240}$" refers to the integrated blood glucose over 240 min.

Compounds useful in the biological assays described herein include the following:

In one aspect, there is provided a pharmaceutical composition which include benzamide-containing peptide compounds described herein (e.g., a peptide compound of Formula (I), (II) or (III)) in combination with a pharmaceutically acceptable excipient. In one aspect, there is provided a pharmaceutical composition which include constrained alkene peptide compounds described herein (e.g., a peptide compound of Formula (IV), (V) or (VI)) as described herein in combination with a pharmaceutically acceptable excipient.

The peptide compounds described herein can be prepared and administered in a wide variety of oral, parenteral, and topical dosage forms. Thus, the compounds of the present invention can be administered by injection (e.g., intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention. The terms "pharmaceutically acceptable excipient" and the like refer to excipients, carriers, other compounding agents and the like which are generally deemed as acceptable for incorporation into a pharmaceutical composition.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in *PHARMACEUTICAL SCIENCES* (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Also provided are drug delivery devices having at least one therapeutically effective dose of the compounds described herein or the pharmaceutical composition containing the compounds described herein. The drug delivery devices can be single or multiple-use vials, single or multiple-use pharmaceutical pens, single or multiple-use cartridges, and the like. In one embodiment, the drug delivery devices contain the compounds or pharmaceutical compositions described herein in amounts capable of providing a patient with from about 7 to about 40 doses or enough doses to last about one week or about one month.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat a specific disease or disorder, such compositions will contain an amount of active ingredient effective to achieve the desired result (e.g., relieving the symptoms of the specific disease or disorder).

For example, the therapeutically effective amount of the compounds described herein to treat the diseases described herein will typically be from about 0.01 µg to about 5 mg; about 0.1 µg to about 2.5 mg; about 1 µg to about 1 mg; about 1 µg to about 50 µg; or about 1 µg to about 25 µg. Alternatively, the therapeutically effective amount of the GLP-1 receptor agonist compounds may be from about 0.001 µg to about 100 µg based on the weight of a 70 kg patient; or from about 0.01 µg to about 50 µg based on the weight of a 70 kg patient. These therapeutically effective doses may be administered once/day, twice/day, thrice/day, once/week, biweekly, or once/month, depending on the formulation. The exact dose to be administered is determined, for example, by the formulation, such as an immediate release formulation or an extended release formulation. For transdermal, nasal or oral dosage forms, the dosage may be increased from about 5-fold to about 10-fold. \

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the specific disease responsive to amelioration); presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from a variety of assays, including but not limited to cell culture assays and behavioral assays. Target concentrations will be those concentrations of active compound(s) that are capable of eliciting a biological response in cell culture assay, or eliciting a behavioral response.

Therapeutically effective amounts for use in humans may be determined from animal models. For example, a dose for humans can be formulated to achieve a concentration that has been found to be effective in animals. The dosage in humans can be adjusted by monitoring the underlying specific disease or disorder and adjusting the dosage upwards or downwards, as known in the art and/or as described herein.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: *THE PHARMACOLOGICAL BASIS OF THERAPEUTICS*, Ch.1, p.1, 1975. The exact formulation, route of administration, and dosage can be chosen by the individual physician in view of the patient's condition and the particular method in which the compound is used.

EXAMPLES

The examples below are meant to illustrate certain embodiments of the invention, and not to limit the scope of the invention. Abbreviations: AcCN=acetonitrile; BuOH=butanol; DCM=dichloromethane; DIEA, DIPEA=N,N-diisopropylethylamine; DMA=N,N-dimethylacetamide; DMAP=N,N-dimethylaminopyridine; DMF=N,N-dimethylformamide; DMSO=dimethylsulfoxide; EDC=N-(3-dimethylaminopropyl)-N'-ethylcarbodiimide hydrochloride; EtOAc=Ethyl Acetate; HOBt=1-hydroxybenzotriazole; HPLC=high pressure liquid chromatography; MS=mass-spectrometry; MsCl=methanesulfonylchloride; NMR=nuclear magnetic resonance; TFA=trifluoroacetic acid; THF=tetrahydrofuran; RT=room temperature; LC/MS=liquid chromatography mass spectroscopy; NCS=N-chlorosuccinimde; TMSI=trimethylsilylimidazole; NMM=N-methylmaleimide; IBCF=isobutylchloroformate; LDA=lithium diisopropylamide; Tf=triflate (trifluoromethanesulfonate); CDI=carbonyldiimidazole; DPPA=diphenylphosphoryl azide; HATU=2-(7-Aza-1H-benzotriazole-1-yl)-1,1,3,3-tetramethyluronium hexafluorophosphate; DME=dimethyl ether; Boc32 tert-butoxycarbonyl; NBS=N-bromosuccinimide; EDCI=1-ethyl-3-(3-dimethylaminopropyl) carbodiimide; dppf=1,1'-bis(diphenylphosphino)ferrocene; SEM: 2-(trimethylsilyl)ethoxymethyl; µW: microwave. Starting materials for syntheses described herein are commercially available or can be synthesized by methods known in the art and/or described herein.

Example 1

Synthesis of Reagents for Benzamide Containing Compounds

Compounds useful in the methods and compositions described herein may be synthesized by a variety of routes, including the synthetic route described in Scheme 3 following.

Scheme 3

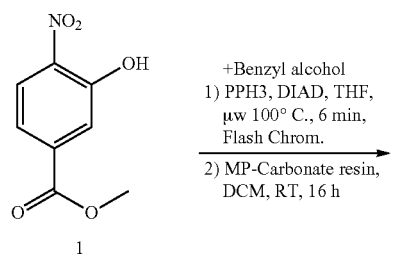

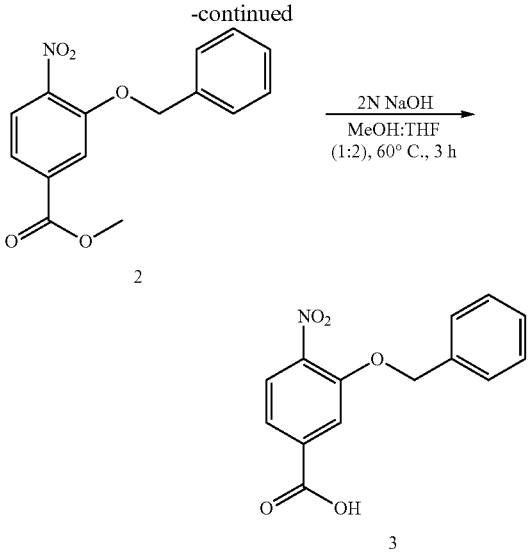

Example 1a

Methyl-3-(benzyloxy)-4-nitrobenzoate (2)

Methyl-3-hydroxy-4-nitrobenzoate Cmpd 1 (1.0 g, 1.0 eq) was dissolved in THF (6 mL) in a microwave vial. Benzyl alcohol (1.0 eq) and $PPh_3$ (1.0 eq) were added to the vial. The reaction vial was put under nitrogen flow, and DIAD (1.0 eq) was added in the dark after stirring the reaction for 1.5 hours. The reaction was microwave irradiated at 100° C. for 6 min (Biotage Initiator™ Eight). The solution was concentrated, and purification of the resultant was performed on a SP1 flash chromatography system (Biotage™) starting with 6% EtOAc: 94% Hex to 60% EtOAc: 40% Hex. The recovered yellow solid was treated with MP-Carbonate resin (2 eq) in DCM and the mixture was shaken overnight at RT. The resin was filtered and multiply washed with DCM. The filtrate was concentrated under vacuum to give Cmpd 2 as a yellow solid (1.39 g, 94% yield).

Example 1b 3-(benzyloxy)-4-nitrobenzoic acid (3)

Cmpd 2 (1.53 g, 1.0 eq) was dissolved in THF (52.8 mL) and MeOH (26.4 mL) in a round bottom flask, followed by addition of 2N NaOH (13.2 mL, 5.0 eq). The reaction was heated at 60° C. for 3 hours, occasionally opening the flask to release pressure. The reaction was monitored by TLC (5% MeOH:95% DCM). The resulting mixture was concentrated, and the residue was dissolved in water and acidified to pH=2-3 with 1N HCl. The acidic solution was extracted with AcOEt 3×, dried over $Na_2SO_4$, filtered and concentrated to afford Cmpd 3 as a light yellowish solid (1.25 g, 96% yield). Analytic: $^1$H NMR (DMSO d6, 500 mHz): δ 7.99 (d, 1H), 7.87 (s, 1H), 7.66 (dd, 1H), 7.46-7.40 (m, 4H), 7.33 (m, 1H), 5.39 (s, 2H). LCMS ($C_{18}$, 2-98% $CH_3CN$ in 0.1% $TFA/H_2O$ over 6 min); Calculated mass for $C_{14}H_{11}NO_5$ (M+H)$^+$274.06. found by LC-MS 274.

By varying the adducted alcohol reagent employed in Scheme 3, a variety of useful reagents is available for synthesis of the compounds described herein. For Cmpds 4, 5, 6 and 7 following (Scheme 4), the alcohols used were iso-butanol, iso-propanol, 2-methyl-naphthol and sec-butanol, respectively. Synthetic conditions were otherwise as provided for Scheme 3.

Scheme 4

Example 1c 3-(isobutyloxy)-4-nitrobenzoic acid (4)

Analytic: $^1$H NMR (DMSO d6, 500 mHz): δ 7.98 (d, 1H), 7.74 (s, 1H), 7.65-7.63 (dd, 1H), 4.00 (d, 2H), 3.9 (s, 3H), 2.02 (hp, 1H), 0.97 (d, 6H). LCMS ($C_{18}$, 2-98% $CH_3CN$ in 0.1% TFA/$H_2O$ over 6 min); Calculated mass for $C_{11}H_{13}NO_5$ (M+H)$^+$ 240.0. found by LC-MS 240.1.

Example 1d 3-(isopropyloxy)-4-nitrobenzoic acid (5)

Analytic: $^1$H NMR (DMSO d6, 500 mHz): δ 7.94 (d, 1H), 7.77 (d, 1H), 7.64-7.62 (dd, 1H), 4.91 (hp, 1H), 1.3 (s, 6H). LCMS (C18, 2-98% $CH_3CN$ in 0.1% TFA/$H_2O$ over 6 min); Calculated mass for $C_{10}H_{11}NO_5$ (M+H)$^+$ 226.0. found by LC-MS 226.1.

Example 1e 3-(naphthylmethyloxy)-4-nitrobenzoic acid (6)

Analytic: $^1$H NMR (DMSO d6, 500 mHz): δ 8.0-7.92 (m, 6H), 7.67 (dd, 1H), 7.58 (dd, 1H), 7.53 (d, 2H), 5.56 (s, 2H). LCMS ($C_{18}$, 2-98% $CH_3CN$ in 0.1% TFA/$H_2O$ over 6 min); Calculated mass for $C_{18}H_{13}NO_5$(M+H)$^+$ 323.0. found by LC-MS 323.8.

Example 1f 3-(secbutyloxy)-4-nitrobenzoic acid (7)

Analytic: $^1$H NMR (DMSO d6, 500 mHz): δ 7.91 (d, 1H), 7.73 (s, 1H), 7.61-7.59 (dd, 1H), 4.72-4.68 (hx, 1H), 1.26 (d, 3H), 0.91 (t, 3H). LCMS ($C_{18}$, 2-98% $CH_3CN$ in 0.1% TFA/$H_2O$ over 6 min); Calculated mass for $C_{11}H_{13}NO_5$ (M+H)$^+$ 240.0. found by LC-MS 240.1.

Example 2

Synthesis of Benzamide Compounds

Preparation of compounds described herein incorporating benzamide and/or polybenzamide moieties generally followed the reaction steps provided in Scheme 5 following.

Scheme 5

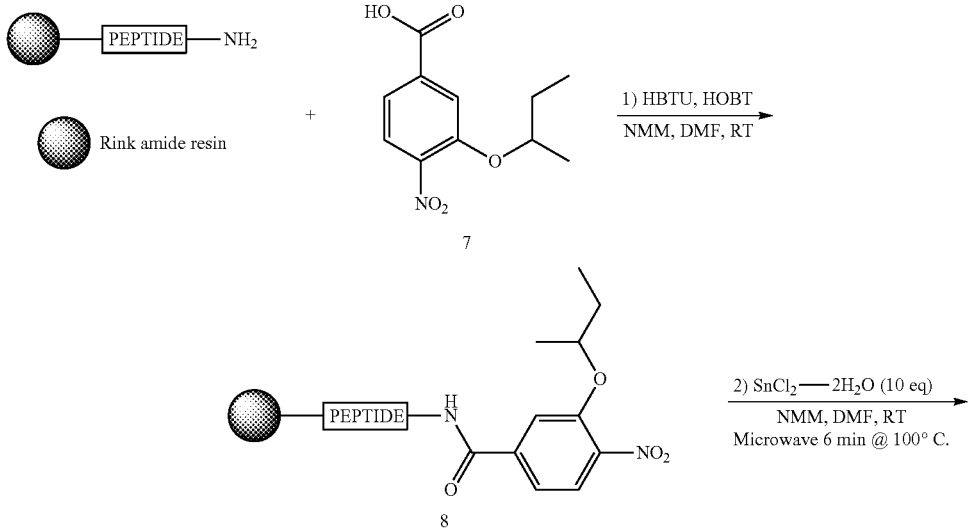

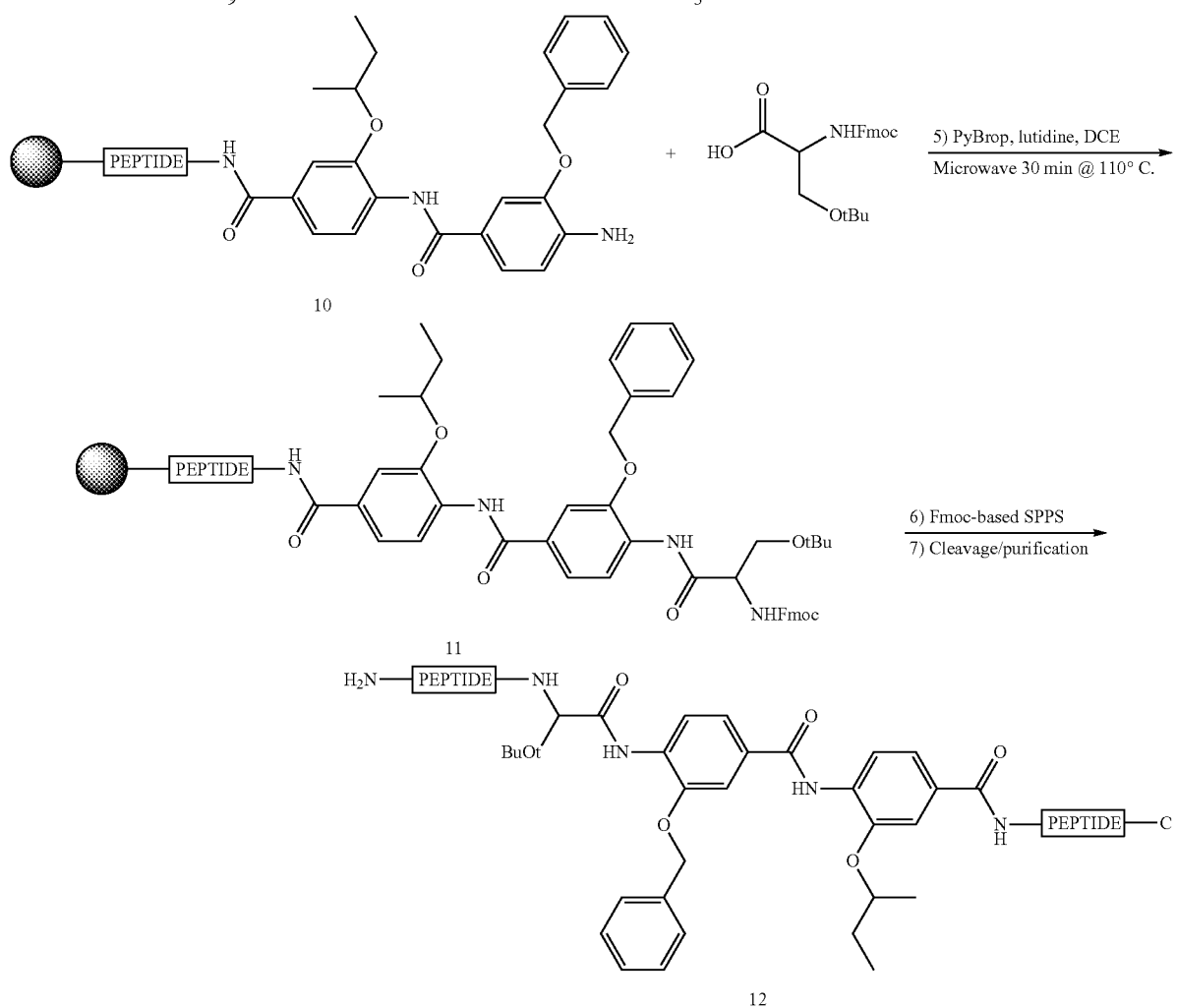

Example 2a

Cmpd 12

Using a combination of automated and manual solid-phase peptide synthesis techniques as described herein in Scheme 5, Cmpd 12 was synthesized as follows.

Step 1.

A calculated 100 μmol of Rink amide resin was weighed into a reaction vessel in a Symphony peptide synthesizer, and the peptide elongation was carried out following standard Fmoc peptide synthesis protocol up to residue Lys[12] of Exendin-4 (1-28). The resulting peptide-resin intermediate (0.3 g, 0.15 mmol) was swollen in DMF. To the slurry was added Cmpd 7 (2.2 eq) followed by HBTU (2.2 eq), HOBt (2.2 eq) and NMM (4.4 eq). After 3 h, the resin was washed with DMF, DCM and MeOH. A chloranil test was negative.

Step 2.

Resin 8 was swollen in DMF for 5-10 minutes followed by addition of $SnCl_2:2H_2O$ (2 M solution) in DMF (10 eq). The slurry was gently stirred for 0.5 hr at RT then microwave irradiated at 100° C. for 6 min (Biotage Initiator™ Eight). Resin 9 was then washed with DMF 6×, DCM 3×, MeOH 2× and dried under high vacuum.

Step 3.

The obtained aniline-Resin 9 was swollen in DCE for 5-10 minutes. To the slurry was added PyBrop (4.8 eq), Lutidine (15 eq) and compound 3 (4 eq). The slurry was gently stirred for 0.5 hr at RT then irradiated with microwaves at 100° C. for 30 min (Biotage Initiator™ Eight). The procedure was repeated.

Step 4.

The reduction of the nitro group of resulting from the previous step to amine was done as described for Step 2 to yield Resin 10.

Step 5.

The coupling of the next amino acid was conducted using PyBrop (4.8 eq), Lutidine (15 eq) and Fmoc-Ser(OtBu)-OH (4 eq). The mixture was then microwave irradiated 100° C. for 30 min (Biotage Initiator8™). The resin was then washed with DMF 4×, DCM 2×, MeOH 3× and dried under high vacuum to afford Resin 11.

Step 6.

A calculated 100 µmol of Resin 11 was weighed into a reaction vessel in a Symphony peptide synthesizer, and the peptide elongation was carried out following standard Fmoc peptide synthesis protocol followed by cleavage of the peptide from the resin with 10 ml TFA/H$_2$O/PhOH/TIPS (95:2:2:1), precipitated by methyl-tent-Butyl ether. The resultant was dissolved and applied to a reverse-phase HPLC column (C$_{18}$, 5-95% CH$_3$CN in 0.1% TFA/H$_2$O over 40 min gradient) to afford Cmpd 12 as a white powder (2.4 mg, 3%). Analytic: Retention time in RP-HPLC (C$_{18}$, 5-75% CH$_3$CN in 0.1% TFA/H$_2$O over 15 min) is 9.62 min; calculated mass for C$_{144}$H$_{213}$N$_{35}$O$_{39}$ (M+H)$^+$ 3058.51. found by LC-MS 1020.6 (M+3H)$^{3+}$, 765.4 (M+4H)$^{4+}$, 1530.8 (M+2H)$^{2+}$.

Using the procedures described for Scheme 5, the following compounds were synthesized.

Example 2b

Cmpd 13

Analytic: Reverse-phase HPLC column (C$_{18}$, 5-95% CH$_3$CN in 0.1% TFA/H$_2$O over 40 min gradient) of Cmpd 13: white powder, 18.3 mg, 12%; retention time in RP-HPLC (C$_{18}$, 5-90% CH$_3$CN in 0.1% TFA/H$_2$O over 5 min): 2.68 min; calculated mass for C$_{145}$H$_{214}$N$_{36}$O$_{42}$ (M+H)$^+$ 3133.54. found by LC-MS 1045.6 (M+3H)$^{3+}$, 784.4 (M+4H)$^{4+}$, 1567.9 (M+2H)$^{2+}$.

Example 2c

Cmpd 14

Analytic: Reverse-phase HPLC column (C$_{18}$, 5-95% CH$_3$CN in 0.1% TFA/H$_2$O over 40 min gradient) of Cmpd 14: white powder, 2.7 mg, 3%; retention time in RP-HPLC (C$_{18}$, 5-95% CH$_3$CN in 0.1% TFA/H$_2$O over 4 min): 3.03 min; calculated mass for C$_{142}$H$_{207}$N$_{33}$O$_{41}$ (M+H)$^+$ 3032.43. found by LC-MS 1012.6 (M+3H)$^{3+}$, 1517.8 (M+2H)$^{2+}$.

Example 2d

Cmpd 15

Analytic: Reverse-phase HPLC column (C$_{18}$, 5-95% CH$_3$CN in 0.1% TFA/H$_2$O over 40 min gradient) of Cmpd 15: white powder, 0.35 mg, >1%; retention time in RP-HPLC (C$_{18}$, 5-95% CH$_3$CN in 0.1% TFA/H$_2$O over 4 min): 3.12 min; calculated mass for C$_{136}$H$_{192}$N$_{30}$O$_{35}$ (M+H)$^+$ 2807.23. found by LC-MS 937.5 (M+3H)$^{3+}$, 1404.8 (M+2H)$^{2+}$.

Example 2e

Cmpd 16

Analytic: Reverse-phase HPLC column (C$_{18}$, 5-95% CH$_3$CN in 0.1% TFA/H$_2$O over 40 min gradient) of Cmpd 16: white powder, 0.4 mg, >1%; retention time in RP-HPLC (C$_{18}$, 10-60% CH$_3$CN in 0.1% TFA/H$_2$O over 35 min):17.02 min; calculated mass for C$_{94}$H$_{127}$N$_{23}$O$_{24}$ (M+H)$^+$ 1963.20. found by LC-MS 1965.1 (M+1), 982.5 (M+2H)$^{2+}$.

Example 2f

Cmpd 17

Analytic: Reverse-phase HPLC column (C$_{18}$, 5-95% CH$_3$CN in 0.1% TFA/H$_2$O over 40 min gradient) of Cmpd 17: white powder, 0.35 mg, >1%; retention time in RP-HPLC (C$_{18}$, 10-60% CH$_3$CN in 0.1% TFA/H$_2$O over 35 min): 21.45 min; calculated mass for C$_{122}$H$_{164}$N$_{26}$O$_{37}$ (M+H)$^+$ 2586.82. found by LC-MS 1294.7 (M+2H)$^{2+}$.

Example 2g

Cmpd 18

Analytic: Reverse-phase HPLC column (C$_{18}$, 5-95% CH$_3$CN in 0.1% TFA/H$_2$O over 40 min gradient) of Cmpd 18: white powder, 0.4 mg, 1%; retention time in RP-HPLC (C$_{18}$, 10-60% CH$_3$CN in 0.1% TFA/H$_2$O over 35 min): 18.79 min; calculated mass for C$_{89}$H$_{118}$N$_{22}$O$_{23}$ (M+H)$^+$ 1864.07. found by LC-MS 1866.0 (M+1), 933.5 (M+2H)$^{2+}$.

Example 3

Biological Activity Assays

Cmpds 12-18

In vitro assay of the biological activity of benzamide-containing compounds was conducted with the GLP-1 cyclase assay as described herein. As shown in Table 3, the most active compounds (Cmpds 13-14) demonstrate nanomolar activity.

TABLE 3

| Cyclase GLP-1 EC$_{50}$ (nm) | |
| --- | --- |
| Cmpd No. | EC$_{50}$ (nm) |
| 12 | 65 |
| 13 | 1.7 |
| 14 | 5.5 |
| 15 | 277 |
| 16 | 136 |
| 17 | 236 |
| 18 | 21 |

In vivo assays for the effect of compound administration on blood glucose were conducted by the methods described herein. As shown in FIG. 1, Cmpds 13-14 were effective in lowering blood glucose as determined by the glucose assay described herein.

Example 4

Synthesis Via Ring Closing Metathesis

Preparation of compounds described herein incorporating RCM generally followed a combination of manual and automated SPPS procedures. A typical schematic scheme is shown in Scheme 6 following.

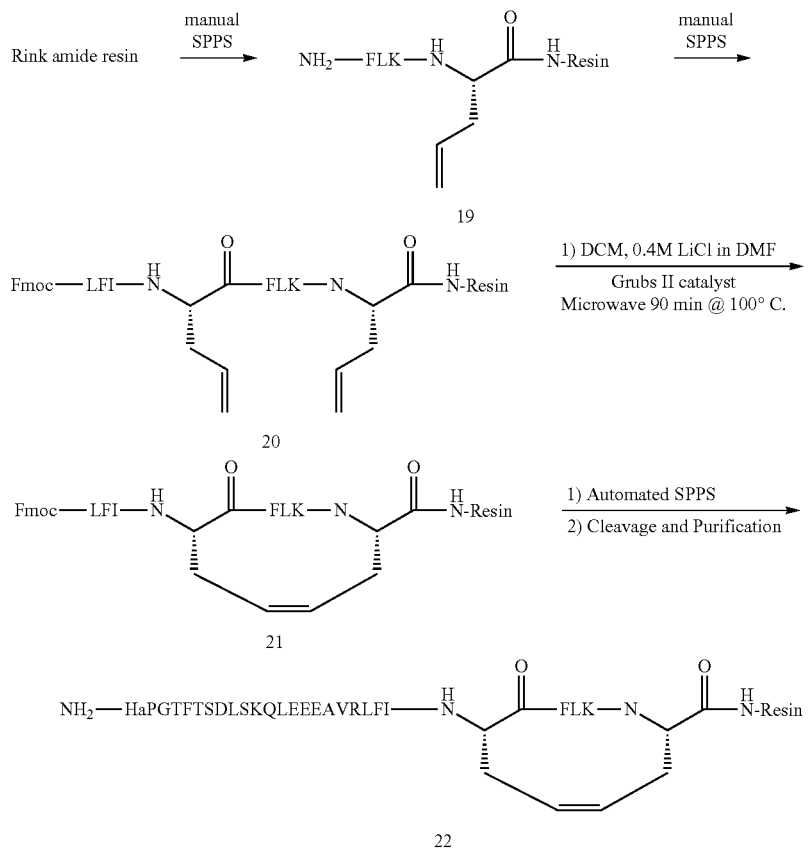

Scheme 6

Example 4a

Cmpd 22

Using a combination of automated and manual solid-phase peptide synthesis techniques as described in Scheme 6, Cmpd 22 was synthesized as follows.

Step 1.

Rink amide resin (0.8 g, 0.512 mmol) was swollen in DMF, treated with 20% piperidine in DMF 2×25 min and washed with DMF 6×. To the slurry was added Fmoc-L-allylGly-OH (0.38 g, 2.2 eq), followed by HBTU (0.430 g, 2.2 eq), HOBt (0.15 g, 2.2 eq) and NMM (0.25 mL, 4.4 eq). After 2 h, the resin was washed with DMF 6×, treated with 20% piperidine in DMF 2×25 min and washed with DMF 6×. The SPPS cycle was repeated with Fmoc-Lys(Boc)-OH, Fmoc-Leu-OH, Fmoc-Phe-OH to afford resin 19.

Step 2.

The resulting resin 19 (0.5 g, 0.31 mmol) was treated with Fmoc-L-allylGly-OH using the same ratio of activators and base. The cycle was repeated with Fmoc-Ile-OH, Fmoc-Phe-OH and Fmoc-Leu-OH to afford resin 20 which was washed and dried.

Step 3.

The dried resin 20 was loaded in a 10-20 mL microwave vessel (Biotage™), swollen with DCM (8 mL) followed by addition of 0.4 M LiCl in DMF (1 mL). The mixture was purged with argon followed by addition of approximately 50 mg (20 mol %) of Grubbs II catalyst, added under a gentle stream of Argon. The catalyst was completely washed down from the vial's walls with DCM (1 mL). The vial was capped, purged with Argon and sonicated for 3-4 min followed by microwave reaction at 100° C. for 90 min in a Biotage Initiator™ Eight. A small sample of resin 21 was cleaved and LCMS analysis showed complete cyclization.

Step 4.

A calculated 100 μmol of resin 21 was weighed into a reaction vessel in a Symphony peptide synthesizer, and the peptide elongation was carried out following standard Fmoc peptide synthesis protocol followed by cleavage of the peptide from the resin with 10 ml TFA/H$_2$O/PhOH/TIPS (95:2:2:1), precipitated by methyl-tent-butyl ether. The resulting residue applied to a reverse-phase HPLC column (C$_{18}$, 20-50% CH$_3$CN in 0.1% TFA/H$_2$O over 30 min gradient) to afford Cmpd 22 as a white powder (20.5 mg, 14%). Analytic: Retention time in RP-HPLC (C$_{18}$, 5-90% CH$_3$CN in 0.1% TFA/H$_2$O over 5 min) is 2.69 min; calculated mass for C$_{145}$H$_{225}$N$_{37}$O$_{41}$ (M+H)$^+$ 3142.63. found by LC-MS 1048.6 (M+3H)$^{3+}$, 1572.9 (M+2H)$^{2+}$.

By using the procedures described for Scheme 6, and employing allylglycine reagents of differing chirality, the following compounds were synthesized.

Example 4b

Cmpd 23

Analytic: Yield: 2.4 mg, 1.5%; retention time in RP-HPLC (C18, 5-90% CH$_3$CN in 0.1% TFA/H$_2$O over 5 min): 2.67 min; calculated mass for $C_{145}H_{225}N_{37}O_{41}$ (M+H)$^+$ 3142.63. found by LC-MS 1048.6 (M+3H)$^{3+}$, 1572.9 (M+2H)$^{2+}$.

Example 4c

Cmpd 24

Analytic: Yield: 34 mg, 22%; retention time in RP-HPLC ($C_{18}$, 5-90% $CH_3CN$ in 0.1% $TFA/H_2O$ over 5 min): 2.68 min; calculated mass for $C_{145}H_{225}N_{37}O_{41}$ (M+H)$^+$ 3142.63. found by LC-MS 1048.6 (M+3H)$^{3+}$, 1572.9 (M+2H)$^{2+}$.

Example 4d

Cmpd 25

Analytic: Yield: 7.2 mg, 7%; retention time in RP-HPLC ($C_{18}$, 5-90% $CH_3CN$ in 0.1% $TFA/H_2O$ over 5 min): 2.68 min; calculated mass for $C_{145}H_{225}N_{37}O_{41}$ (M+H)$^+$ 3142.63. found by LC-MS 1048.6 (M+3H)$^{3+}$, 1572.9 (M+2H)$^{2+}$.

A variety of amino acid reagents incorporating an allyl functionality suitable for ring closing metathesis. In the following two examples, Fmoc-L-β-homoallylGly-OH was employed in the first and/or fifth coupling described in Scheme 6.

Example 4e

Cmpd 26

Yield: 22 mg, 18%; retention time in RP-HPLC ($C_{18}$, 5-90% $CH_3CN$ in 0.1% $TFA/H_2O$ over 5 min): 2.95 min; calculated mass for $C_{146}H_{227}N_{37}O_{41}$ (M+H)$^+$ 3156.66 found by LC-MS 1053.6 (M+3H)$^{3+}$, 1579.9 (M+2H)$^{2+}$, 790.4 (M+4H)$^{4+}$.

Example 4f

Cmpd 27

Yield: 28 mg, 21%; retention time in RP-HPLC ($C_{18}$, 5-90% $CH_3CN$ in 0.1% $TFA/H_2O$ over 5 min): 2.93 min; calculated mass for $C_{147}H_{229}N_{37}O_{41}$ (M+H)$^+$ 3170.69 found by LC-MS 1058.6 (M+3H)$^{3+}$, 1586.9 (M+2H)$^{2+}$, 794.6 (M+4H)$^{4+}$.

Example 5

Synthesis of N-Linked Ring Closing Metathesis Compounds

Example 5a

Cmpd 34

Synthesis of Cmpd 34 followed the synthetic route provided in Scheme 7 following.

Scheme 7

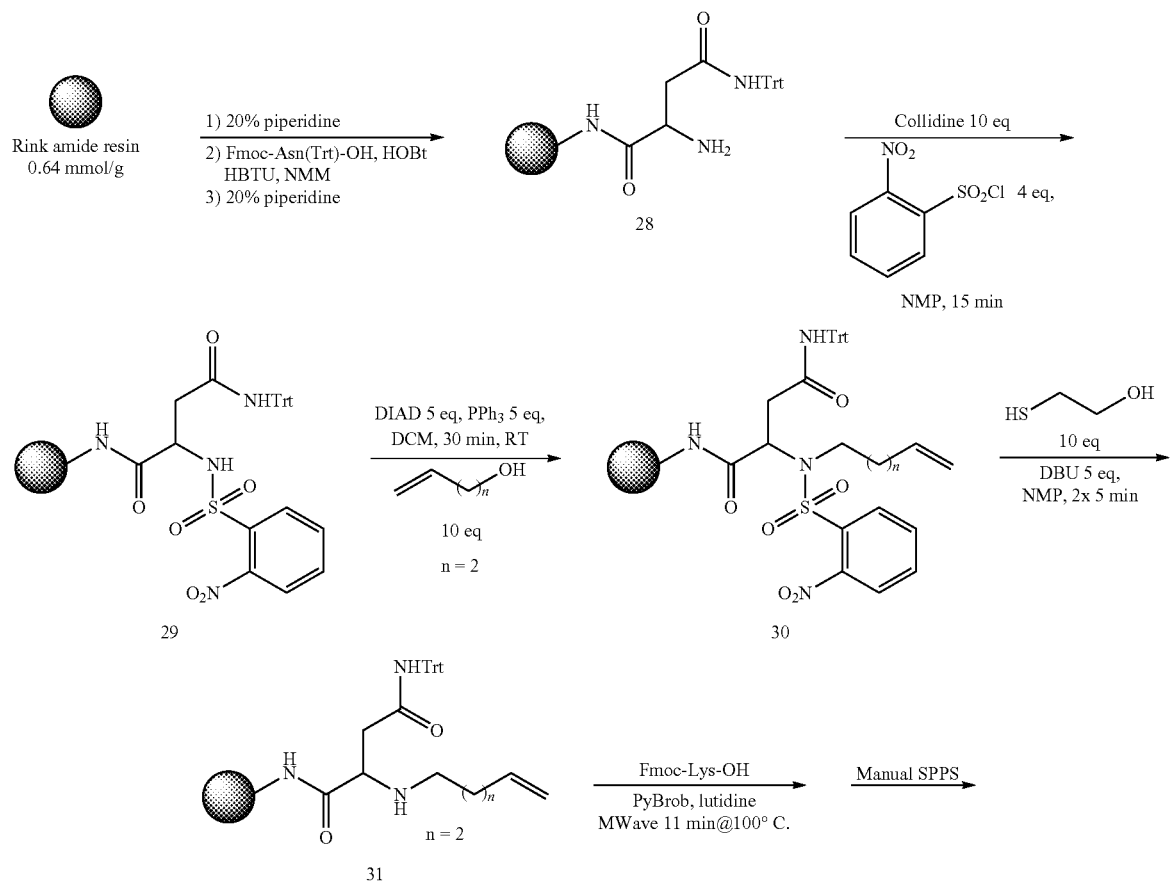

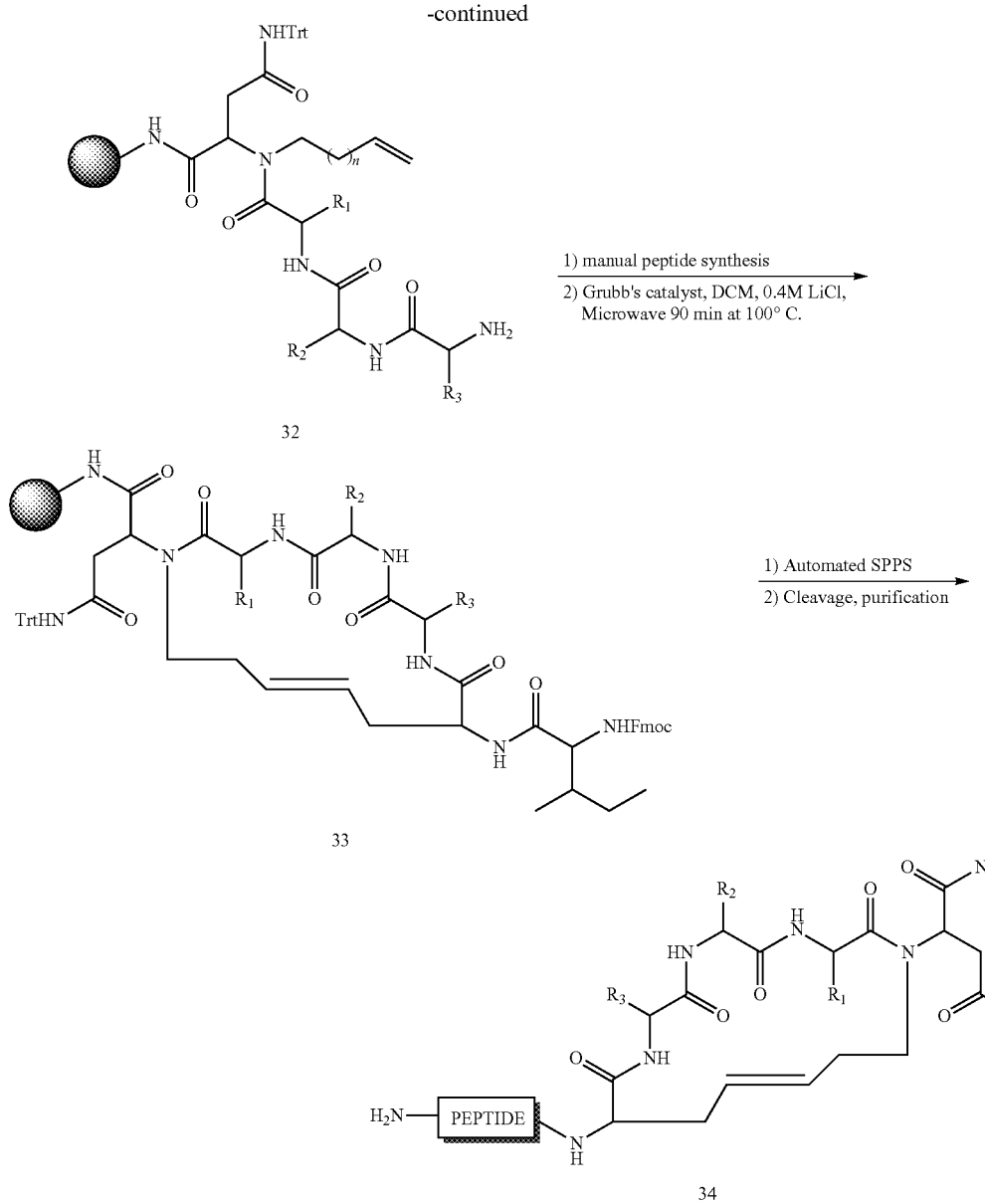

Step 1.

Rink amide resin (0.8 g, 0.512 mmol) was swollen in DMF, treated with 20% piperidine in DMF 2×25 min and washed with DMF 6×. To the slurry was added Fmoc-Asn(Trt)-OH (2.2 eq), followed by HBTU (2.2 eq), HOBt (2.2 eq) and NMM (4.4 eq). After 2 h, the resin was washed with DMF 6×, treated with 20% piperidine in DMF 2×25 min and washed with DMF 6× to afford resin 28.

Step 2.

Resin 28 was swollen in NMP and then treated with 2,4,6-collidine (10 eq) and 2-nitrobenzoyl chloride (4 eq). The reaction was shaken at room temperature for 25 min. The resin was then washed with NMP 3×, DMF 2×, DCM 2× to yield resin 29.

Step 3.

Resin 29 was swollen in dry THF followed by addition of $PPh_3$ (5 eq) and 3-buten-1-ol (10 eq), and subsequent dropwise addition, in low light, of DIAD (5 eq) under a gentle stream of Argon. The slurry was shaken at room temperature for 35 min then washed with THF 3×, DMF 3×, NMP 3× to afford resin 30.

Step 4.

Resin 30 was swollen in NMP followed by addition of DBU (5 eq) and mercaptoethanol (10 eq). The mixture was shaken in a syringe at RT for 5 min, then washed with NMP 1×. The treatment was repeated to afford resin 31 which gave a positive chloranil test.

Step 5. In a microwave vial, resin 31 was swollen in 1,2-DCE followed by addition of Fmoc-Lys(Boc)-OH (4 eq), PyBrop (4.8 eq), 2,6-lutidine (15 eq) and a few drops of DMF. The slurry was microwave irradiated (Biotage Initiator8™) for 11 min at 100° C. Chloranil test was negative, thus the resin was treated with 20% piperidine 2×25 min and washed with DMF 6×. Cleavage of a small resin sample was analyzed by LCMS showing the expected M+1.

Step 6.

The resulting peptide-resin was swollen in DMF and to the slurry was added Fmoc-Leu-OH (2.2 eq), followed by HBTU (2.2 eq), HOBt (2.2 eq) and NMM (4.4 eq). After 2 h, resin 32 was washed with DMF 6×, treated with 20% piperidine in DMF 2×25 min and washed with DMF 6×.

Step 7.

The previous cycle was repeated with Fmoc-Phe-OH, Fmoc-L-allylGly-OH and Fmoc-Leu-OH. The dried resin (0.250 g, 0.139 mmol) was loaded in a 5 mL microwave vessel (Biotage™) and swollen with DCM (2.4 mL), followed by addition of 0.4 M LiCl in DMF (0.7 mL). The mixture was purged with argon followed by addition of approximately 40 mg (20 mol %) of Grubbs II catalyst, added under a gentle stream of Argon. The catalyst was completely washed down from the vial's walls with DCM (0.5 mL). The vial was capped, purged with Argon and sonicated for 3-4 min followed by microwave reaction at 100° C. for 90 min in a Biotage Initiator™ Eight. A small sample of resin 33 was cleaved, and LCMS analysis showed complete cyclization. In the structures depicted in Scheme 7, substituents $R_1$, $R_2$ and $R_3$ refer to the side chains of Lys, Leu and Phe, respectively.

Step 8.

A calculated 100 μmol of resin 33 was weighed into a reaction vessel in a Symphony peptide synthesizer, and the peptide elongation was carried out following standard Fmoc peptide synthesis protocol, followed by cleavage of the peptide from the resin with 10 ml TFA/H$_2$O/PhOH/TIPS (95:2:2:1), precipitated by methyl-tent-Butyl ether. The resulting peptide was dissolved in 1.5 mL of MeOH:ACN (1:1), followed by addition of 2 M LiOH (0.6 mL) and the reaction stirred at RT for 6 h. The resultant was dissolved and applied to a reverse-phase HPLC column (C$_{18}$, 5-95% CH$_3$CN in 0.1% TFA/H$_2$O over 40 min gradient) to afford Cmpd 34 as a white powder. Analytic: Yield: 16.6 mg, 11%; retention time in RP-HPLC (C$_{18}$, 5-90% CH$_3$CN in 0.1% TFA/H$_2$O over 5 min): 2.89 min; calculated mass for C$_{148}$H$_{230}$N$_{38}$O$_{42}$ (M+H)$^+$ 3213.71. found by LC-MS 1072.6 (M+3H)$^{3+}$, 804.4 (M+4H)$^{4+}$, 1608.9 (M+2H)$^{2+}$.

Example 5b

Cmpd 35

The synthesis of Cmpd 35 followed the procedure described for Scheme 7, with the exception that Fmoc-L-β-homoallylGly-OH was used instead of Fmoc-L-allylGly-OH in the fourth coupling. After cleavage, the crude was dissolved and applied to a reverse-phase HPLC column (C$_{18}$, 5-95% CH$_3$CN in 0.1% TFA/H$_2$O over 40 min gradient) to afford Cmpd 35 as a white powder. Analytic: Yield: 22.1 mg, 13%; retention time in RP-HPLC (C$_{18}$, 5-90% CH$_3$CN in 0.1% TFA/H$_2$O over 5 min): 2.92 min; calculated mass for C$_{149}$H$_{232}$N$_{38}$O$_{42}$ (M+H)$^+$ 3227.74. found by LC-MS 1077.6 (M+3H)$^{3+}$, 808.4 (M+4H)$^{4+}$, 1614.9 (M+2H)$^{2+}$.

Example 5c

Cmpd 36

The synthesis of Cmpd 35 followed the procedure described for Scheme 7, with the exception that allyl alcohol was employed in the Mitsunobu alkylation step (Step 3). After cleavage, the crude was dissolved and applied to a reverse-phase HPLC column (C$_{18}$, 5-95% CH$_3$CN in 0.1% TFA/H$_2$O over 40 min gradient) to afford Cmpd 36 as a white powder. Analytic: Yield: 12.1 mg, 9%; retention time in RP-HPLC (C$_{18}$, 10-90% CH$_3$CN in 0.1% TFA/H$_2$O over 30 min): 17.68 min; calculated mass for C$_{147}$H$_{228}$N$_{38}$O$_{42}$ (M+H)$^+$ 3199.69. found by LC-MS 1067.6 (M+3H)$^{3+}$, 801.4 (M+4H)$^{4+}$, 1601.9 (M+2H)$^{2+}$.

Example 6

Glucose Lowering Biological Activity In Vivo

In vitro assay of the biological activity of constrained alkene compounds was conducted with the GLP-1 cyclase assay as described herein. As shown in Table 4, the most active compounds (Cmpds 27 and 34) demonstrate subnanomolar activity, and Cmpd 22 has nanomolar activity.

TABLE 4

| Cyclase GLP-1 $EC_{50}$ (nm) | |
| --- | --- |
| Cmpd No. | $EC_{50}$ (nm) |
| 22 | 5 |
| 23 | 133 |
| 24 | 127 |
| 25 | 131 |
| 26 | 35 |
| 27 | 0.8 |
| 34 | 0.7 |
| 35 | 35 |

Figure 2:
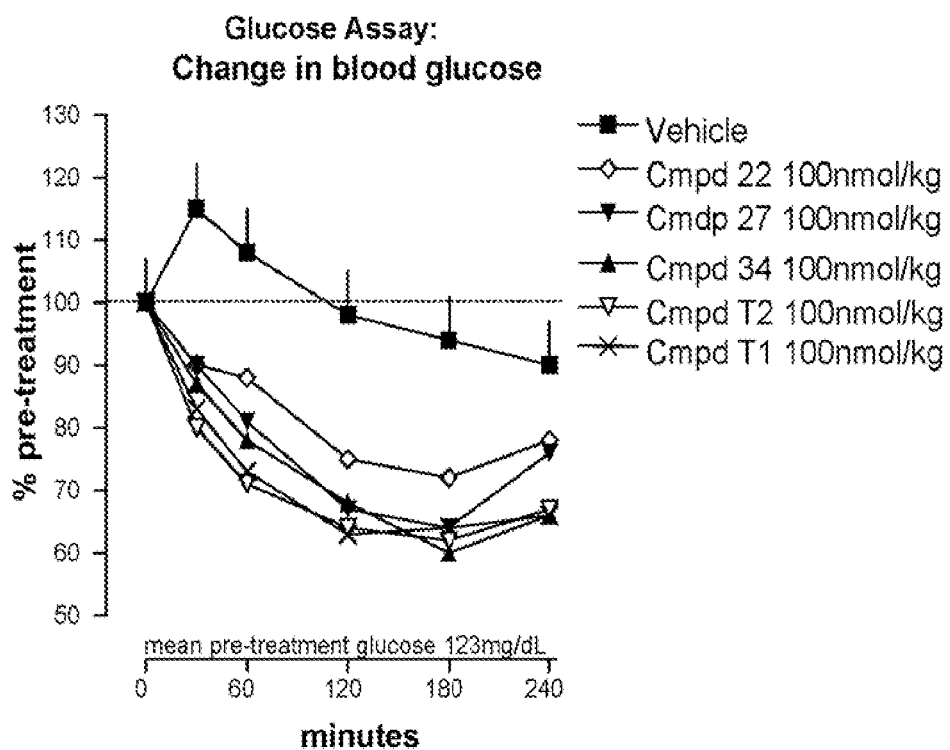
FIG. 2 depicts the time course of blood glucose concentration as a percentage of pre-treatment levels, for certain alkenylenyl-containing compounds described herein. Experimental conditions were the same as those described for FIG. 1. Legend: Vehicle (closed box); Cmpd 22 (open diamond); Cmpd 27 (close triangle tip down); Cmpd 34 (closed triangle tip up); Cmpd T2 (open triangle); Cmpd T1 (cross).

In vivo assays for the effect of compound administration on blood glucose were conducted by the methods described herein. As shown in FIG. 2, all of the tested compounds were effective in lowering blood glucose as determined by the glucose assay described herein.

Example 7

Molecular Modeling Studies of Benzamide-Contained Compounds

Figure 3:
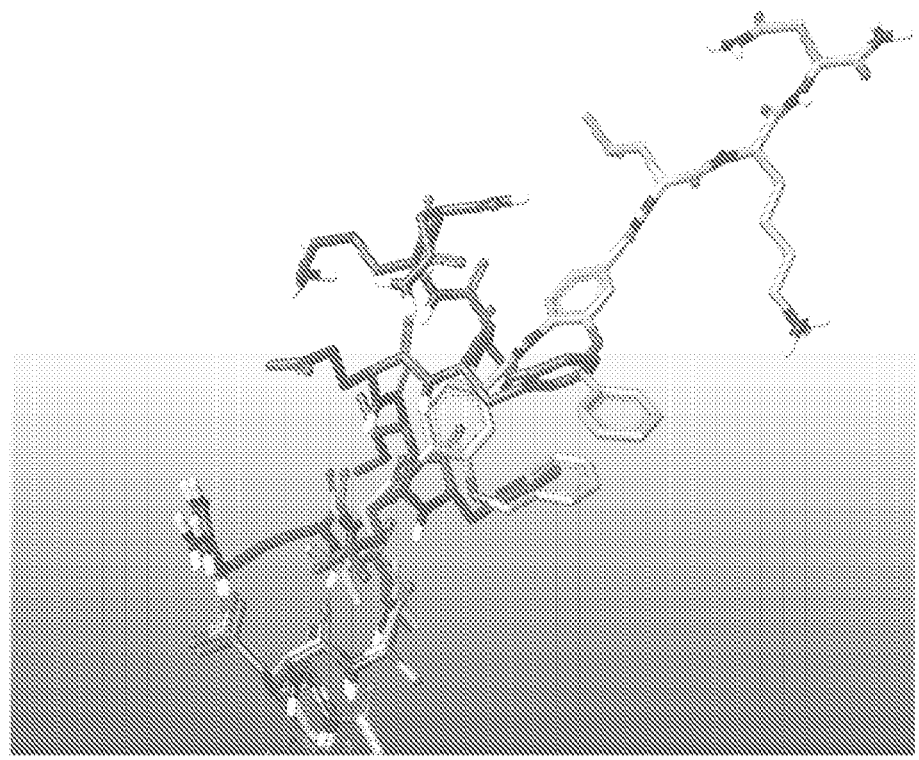
FIG. 3 depicts the results of molecular modeling studies of the overlap available between the side chains of Cmpd T1 and the side chain surrogate moieties of Cmpd 13.

A molecular modeling study was conducted to assess the common conformational space, and energetics thereof, for the side chains of Cmpd T1 and the corresponding side chain surrogate moieties of Cmpd 13. As shown in FIG. 3, an essentially perfect overlap is observed in the minimum energy structures of the two side chain surrogate phenyl rings of Cmpd 13 compared with the corresponding Phe groups of Cmpd T1.

Example 8

Molecular Modeling Studies of Constrained Alkene Compounds

Figure 4:
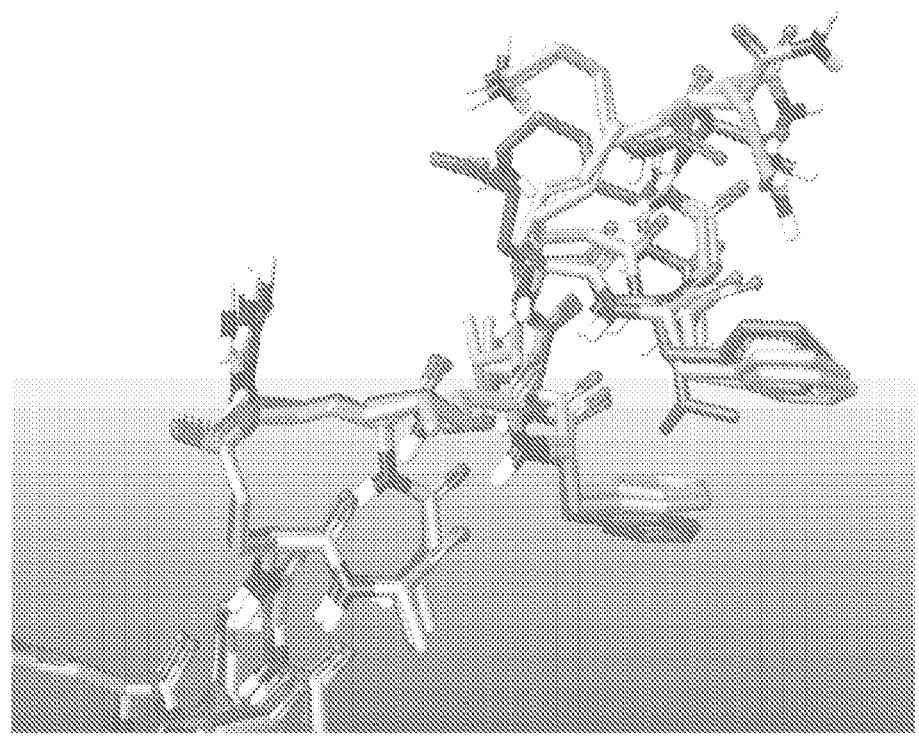
FIG. 4 depicts the results of molecular modeling studies of the overlap available between the side chains of Cmpd T1 and the side chain surrogate moieties of Cmpd 27 and Cmpd 34.

A molecular modeling study was conducted to assess the common conformational space, and energetics thereof, for the side chains of Cmpd T1 and the corresponding side chain surrogate moieties of Cmpd 27 and Cmpd 34. As shown in FIG. 4, an essentially perfect overlap is observed in the minimum energy structures of the two side chain surrogate phenyl rings of Cmpd 27 and Cmpd 34 compared with the corresponding Phe groups of Cmpd T1.

What is claimed is:
1. A compound selected from the group consisting of:
compound 12
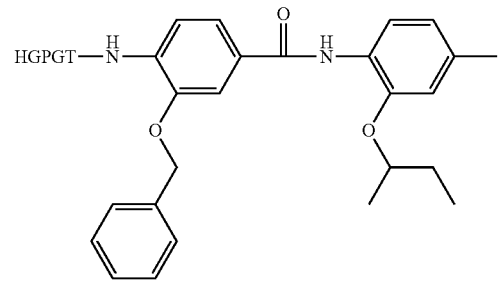
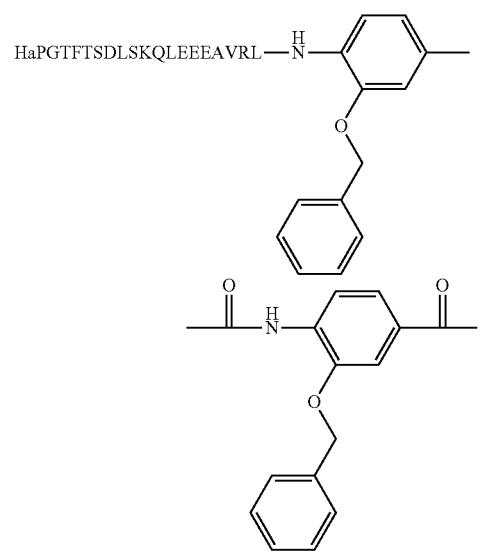
compound 13
compound 14
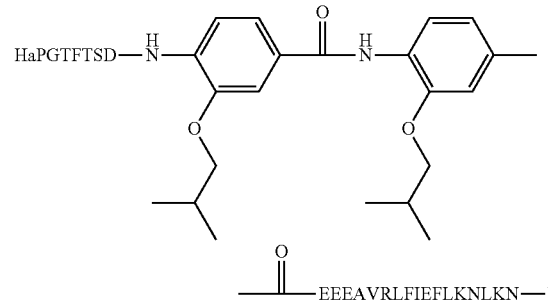
compound 15
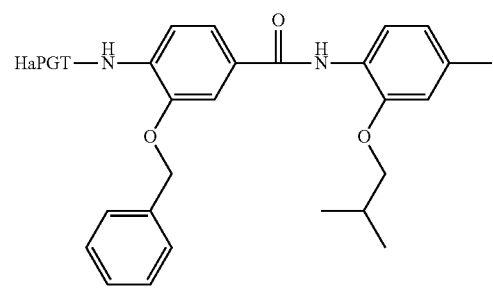
-continued
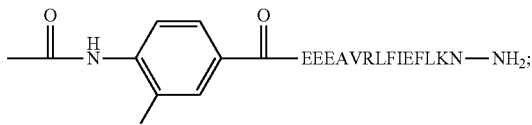
compound 16
compound 17
compound 18
compound 22
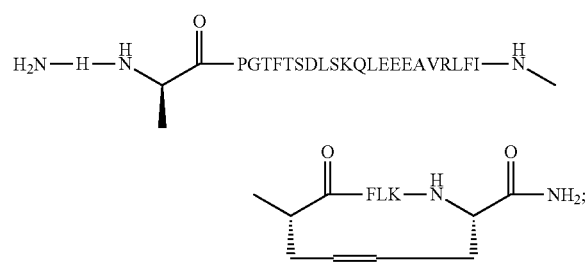

-continued
compound 23
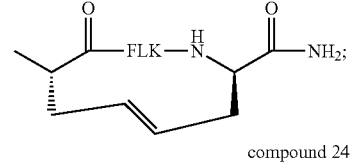
compound 24
compound 25
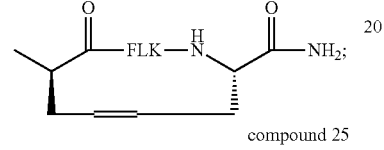
compound 26
compound 27
-continued
compound 34
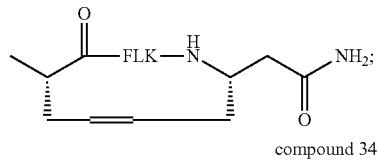
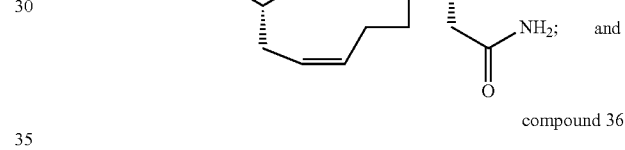
compound 35
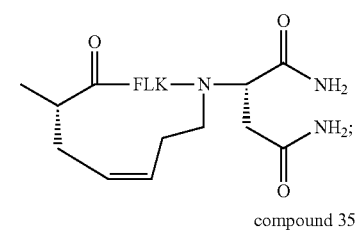
compound 36
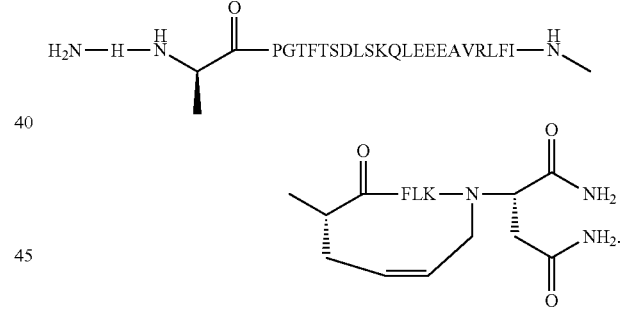
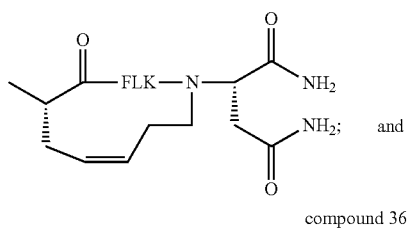
2. A pharmaceutical composition comprising a compound of claim 1 and a pharmaceutically acceptable carrier.
* * * * *

SEQUENCE LISTING

<160> NUMBER OF SEQ ID NOS: 49

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: His, absent or a non-standard amino acid
      structure "Y1"
<220> FEATURE:
<221> NAME/KEY: MOD_RES
<222> LOCATION: (2)..(2)
<223> OTHER INFORMATION: Gly, Ala, D-Ala or Aib
<220> FEATURE:
<221> NAME/KEY: MOD_RES
<222> LOCATION: (3)..(3)
<223> OTHER INFORMATION: Gly, Ala, D-Ala, Aib, Glu, Pro or a
      non-standard amino acid structure "Y1"
<220> FEATURE:
<221> NAME/KEY: MOD_RES
<222> LOCATION: (14)..(14)
<223> OTHER INFORMATION: Met or Leu
<220> FEATURE:
<221> NAME/KEY: MOD_RES
<222> LOCATION: (25)..(25)
<223> OTHER INFORMATION: Trp or Phe
<220> FEATURE:
<221> NAME/KEY: misc_feature
<222> LOCATION: (29)..(39)
<223> OTHER INFORMATION: This region may encompass "Gly Gly" or "Gly Gly
      Pro Ser Ser Gly Ala Pro Pro Pro Ser" and is 2 or 11 residues
      in length or is absent
<220> FEATURE:
<223> OTHER INFORMATION: C-term OH or NH2

<400> SEQUENCE: 1

Xaa Xaa Xaa Gly Thr Phe Thr Ser Asp Leu Ser Lys Gln Xaa Glu Glu
1               5                   10                  15

Glu Ala Val Arg Leu Phe Ile Glu Xaa Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(39)
<223> OTHER INFORMATION: At least one pair of residues in this sequence
      may be linked with an alkenylenyl bridge or an alkylenyl bridge
<220> FEATURE:
<221> NAME/KEY: MOD_RES
<222> LOCATION: (1)..(1)
<223> OTHER INFORMATION: His, absent or a non-standard amino acid
      structure "Y1"
<220> FEATURE:
<221> NAME/KEY: MOD_RES
<222> LOCATION: (2)..(2)
<223> OTHER INFORMATION: Gly, Ala, D-Ala or Aib
<220> FEATURE:
<221> NAME/KEY: MOD_RES
<222> LOCATION: (3)..(3)
<223> OTHER INFORMATION: Gly, Ala, D-Ala, Aib, Glu, Pro or a
      non-standard amino acid structure "Y1"

```
<220> FEATURE:
<221> NAME/KEY: MOD_RES
<222> LOCATION: (14)..(14)
<223> OTHER INFORMATION: Met or Leu
<220> FEATURE:
<221> NAME/KEY: MOD_RES
<222> LOCATION: (25)..(25)
<223> OTHER INFORMATION: Trp or Phe
<220> FEATURE:
<221> NAME/KEY: misc_feature
<222> LOCATION: (29)..(39)
<223> OTHER INFORMATION: This region may encompass "Gly Gly" or "Gly Gly
      Pro Ser Ser Gly Ala Pro Pro Pro Ser" and is 2 or 11 residues
      in length or is absent
<220> FEATURE:
<223> OTHER INFORMATION: C-term OH or NH2

<400> SEQUENCE: 2

Xaa Xaa Xaa Gly Thr Phe Thr Ser Asp Leu Ser Lys Gln Xaa Glu Glu
1               5                   10                  15

Glu Ala Val Arg Leu Phe Ile Glu Xaa Leu Lys Asn Gly Gly Pro Ser
            20                  25                  30

Ser Gly Ala Pro Pro Pro Ser
        35

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<223> OTHER INFORMATION: C-term NH2

<400> SEQUENCE: 3

His Ala Pro Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 4

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: C-term OH

<400> SEQUENCE: 5

Gly Gly Pro Ser Ser Gly Ala Pro Pro Pro Ser
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 6

Gly Gly Pro Ser Ser Gly Ala Pro Pro Pro Ser
1               5                   10

<210> SEQ ID NO 7
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: His, absent or a non-standard amino acid
      structure "Y1"
<220> FEATURE:
<221> NAME/KEY: MOD_RES
<222> LOCATION: (2)..(2)
<223> OTHER INFORMATION: Gly, Ala, D-Ala or Aib
<220> FEATURE:
<221> NAME/KEY: MOD_RES
<222> LOCATION: (3)..(3)
<223> OTHER INFORMATION: Gly, Ala, D-Ala, Aib, Glu, Pro or a
      non-standard amino acid structure "Y1"
<220> FEATURE:
<221> NAME/KEY: MOD_RES
<222> LOCATION: (10)..(13)
<223> OTHER INFORMATION: Individual residues may or may not be present
<220> FEATURE:
<221> NAME/KEY: MOD_RES
<222> LOCATION: (14)..(14)
<223> OTHER INFORMATION: Met or Leu
<220> FEATURE:
<221> NAME/KEY: MOD_RES
<222> LOCATION: (15)..(15)
<223> OTHER INFORMATION: May or may not be present
<220> FEATURE:
<221> NAME/KEY: MOD_RES
<222> LOCATION: (16)..(17)
<223> OTHER INFORMATION: Glu or Ala
<220> FEATURE:
<221> NAME/KEY: MOD_RES
<222> LOCATION: (19)..(21)
<223> OTHER INFORMATION: Individual residues may or may not be present
<220> FEATURE:
<221> NAME/KEY: MOD_RES
<222> LOCATION: (22)..(22)
<223> OTHER INFORMATION: Non-standard amino acid structure "Y1"
<220> FEATURE:
<221> NAME/KEY: misc_feature
<222> LOCATION: (23)..(33)
<223> OTHER INFORMATION: This region may encompass "Gly Gly" or "Gly Gly
      Pro Ser Ser Gly Ala Pro Pro Pro Ser" and is 2 or 11 residues
      in length or is absent
<220> FEATURE:
<223> OTHER INFORMATION: C-term OH or NH2

<400> SEQUENCE: 7
```

```
Xaa Xaa Xaa Gly Thr Phe Thr Ser Asp Leu Ser Lys Gln Xaa Glu Xaa
1               5                   10                  15

Xaa Ala Val Arg Leu Xaa Gly Gly Pro Ser Ser Gly Ala Pro Pro Pro
            20                  25                  30

Ser

<210> SEQ ID NO 8
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: His, absent or a non-standard amino acid
      structure "Y1"
<220> FEATURE:
<221> NAME/KEY: MOD_RES
<222> LOCATION: (2)..(2)
<223> OTHER INFORMATION: Gly, Ala, D-Ala or Aib
<220> FEATURE:
<221> NAME/KEY: MOD_RES
<222> LOCATION: (3)..(3)
<223> OTHER INFORMATION: Gly, Ala, D-Ala, Aib, Glu, Pro or a
      non-standard amino acid structure "Y1"
<220> FEATURE:
<221> NAME/KEY: MOD_RES
<222> LOCATION: (6)..(14)
<223> OTHER INFORMATION: This region may be 4 to 6 residues in length
      spanning nine positions and encompassing the following sequences:
      "Phe Thr Ser Y1," "Phe Y1 Gln Met," "Phe Thr Y1 Met," "Y1 Lys
      Gln Met," "Phe Y1 Gln Leu," "Phe Thr Y1
<220> FEATURE:
<221> NAME/KEY: MOD_RES
<222> LOCATION: (6)..(14)
<223> OTHER INFORMATION: continued from above; Leu," "Y1 Lys Gln Leu,"
      "Y1 Ser Lys Gln Met," "Phe Y1 Lys Gln Met," "Phe Thr
      Y1 Gln Met," "Phe Thr Ser Y1 Met," "Phe Thr Ser
      Asp Y1," "Y1 Ser Lys Gln Leu," "Phe Y1 Lys Gln
<220> FEATURE:
<221> NAME/KEY: MOD_RES
<222> LOCATION: (6)..(14)
<223> OTHER INFORMATION: continued from above; Leu," "Phe Thr Y1 Gln
      Leu," "Phe Thr Ser Y1 Leu," "Phe Thr Ser Asp Leu Y1," "Phe
      Thr Ser Asp Y1 Met," "Phe Thr Ser Y1 Gln Met," "Phe
      Thr Y1 Lys Gln Met," "Phe Y1 Ser Lys Gln Met," "Y1
<220> FEATURE:
<221> NAME/KEY: MOD_RES
<222> LOCATION: (6)..(14)
<223> OTHER INFORMATION: continued from above; Leu Ser Lys Gln Met,"
      "Phe Thr Ser Asp Y1 Leu," "Phe Thr Ser Y1 Gln Leu," "Phe Thr
      Y1 Lys Gln Leu," "Phe Y1 Ser Lys Gln Leu" or "Y1 Leu
      Ser Lys Gln Leu," wherein 'Y1' is a non-standard
<220> FEATURE:
<221> NAME/KEY: MOD_RES
<222> LOCATION: (6)..(14)
<223> OTHER INFORMATION: continued from above; amino acid structure and
      some positions may be absent
<220> FEATURE:
<221> NAME/KEY: MOD_RES
<222> LOCATION: (15)..(15)
<223> OTHER INFORMATION: May or may not be present
<220> FEATURE:
<221> NAME/KEY: MOD_RES
<222> LOCATION: (16)..(17)
<223> OTHER INFORMATION: Glu or Ala
<220> FEATURE:
<221> NAME/KEY: MOD_RES
<222> LOCATION: (25)..(25)
<223> OTHER INFORMATION: Trp or Phe
<220> FEATURE:
<221> NAME/KEY: misc_feature
<222> LOCATION: (29)..(39)
```

```
<223> OTHER INFORMATION: This region may encompass "Gly Gly" or "Gly Gly
      Pro Ser Ser Gly Ala Pro Pro Pro Ser" and is 2 to 11 residues
      in length or is absent
<220> FEATURE:
<223> OTHER INFORMATION: C-term OH or NH2

<400> SEQUENCE: 8

Xaa Xaa Xaa Gly Thr Xaa Xaa Xaa Xaa Xaa Xaa Xaa Xaa Glu Xaa
1               5                   10                  15

Xaa Ala Val Arg Leu Phe Ile Glu Xaa Leu Lys Asn Gly Gly Pro Ser
            20                  25                  30

Ser Gly Ala Pro Pro Pro Ser
        35

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-standard amino acid structure "Y1"

<400> SEQUENCE: 9

Xaa Ser Lys Gln Met
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-standard amino acid structure "Y1"

<400> SEQUENCE: 10

Phe Xaa Lys Gln Met
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-standard amino acid structure "Y1"

<400> SEQUENCE: 11

Phe Thr Xaa Gln Met
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: A non-standard amino acid structure "Y1"

<400> SEQUENCE: 12

Phe Thr Ser Xaa Met
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: A non-standard amino acid structure "Y1"

<400> SEQUENCE: 13

Phe Thr Ser Asp Xaa
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-standard amino acid structure "Y1"

<400> SEQUENCE: 14

Xaa Ser Lys Gln Leu
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-standard amino acid structure "Y1"

<400> SEQUENCE: 15

Phe Xaa Lys Gln Leu
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-standard amino acid structure "Y1"

<400> SEQUENCE: 16
```

Phe Thr Xaa Gln Leu
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: A non-standard amino acid structure "Y1"

<400> SEQUENCE: 17

Phe Thr Ser Xaa Leu
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: A non-standard amino acid structure "Y1"

<400> SEQUENCE: 18

Phe Thr Ser Asp Leu Xaa
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: A non-standard amino acid structure "Y1"

<400> SEQUENCE: 19

Phe Thr Ser Asp Xaa Met
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: A non-standard amino acid structure "Y1"

<400> SEQUENCE: 20

Phe Thr Ser Xaa Gln Met
1               5

<210> SEQ ID NO 21
<211> LENGTH: 6
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-standard amino acid structure "Y1"

<400> SEQUENCE: 21

Phe Thr Xaa Lys Gln Met
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-standard amino acid structure "Y1"

<400> SEQUENCE: 22

Phe Xaa Ser Lys Gln Met
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-standard amino acid structure "Y1"

<400> SEQUENCE: 23

Xaa Leu Ser Lys Gln Met
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: A non-standard amino acid structure "Y1"

<400> SEQUENCE: 24

Phe Thr Ser Asp Xaa Leu
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
```

```
<223> OTHER INFORMATION: A non-standard amino acid structure "Y1"

<400> SEQUENCE: 25

Phe Thr Ser Xaa Gln Leu
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-standard amino acid structure "Y1"

<400> SEQUENCE: 26

Phe Thr Xaa Lys Gln Leu
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-standard amino acid structure "Y1"

<400> SEQUENCE: 27

Phe Xaa Ser Lys Gln Leu
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-standard amino acid structure "Y1"

<400> SEQUENCE: 28

Xaa Leu Ser Lys Gln Leu
1               5

<210> SEQ ID NO 29
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: A non-standard amino acid residue
<220> FEATURE:
<223> OTHER INFORMATION: C-term NH2

<400> SEQUENCE: 29

His Gly Pro Gly Thr Xaa Xaa Ser Lys Gln Leu Glu Glu Glu Ala Val
```

```
                1               5                   10                  15
Arg Leu Phe Ile Glu Phe Leu Lys Asn
                20                  25

<210> SEQ ID NO 30
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (22)..(23)
<223> OTHER INFORMATION: A non-standard amino acid residue
<220> FEATURE:
<223> OTHER INFORMATION: C-term NH2

<400> SEQUENCE: 30

His Ala Pro Gly Thr Phe Thr Ser Asp Leu Ser Lys Gln Leu Glu Glu
1               5                   10                  15

Glu Ala Val Arg Leu Xaa Xaa Leu Lys Asn
                20                  25

<210> SEQ ID NO 31
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (10)..(11)
<223> OTHER INFORMATION: A non-standard amino acid residue
<220> FEATURE:
<223> OTHER INFORMATION: C-term NH2

<400> SEQUENCE: 31

His Ala Pro Gly Thr Phe Thr Ser Asp Xaa Xaa Glu Glu Glu Ala Val
1               5                   10                  15

Arg Leu Phe Ile Glu Phe Leu Lys Asn
                20                  25

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (6)..(8)
<223> OTHER INFORMATION: A non-standard amino acid residue
<220> FEATURE:
<223> OTHER INFORMATION: C-term NH2

<400> SEQUENCE: 32
```

His Ala Pro Gly Thr Xaa Xaa Xaa Glu Glu Glu Ala Val Arg Leu Phe
1               5                   10                  15

Ile Glu Phe Leu Lys Asn
            20

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(17)
<223> OTHER INFORMATION: A non-standard amino acid residue
<220> FEATURE:
<223> OTHER INFORMATION: C-term NH2

<400> SEQUENCE: 33

His Ala Pro Gly Thr Phe Thr Ser Asp Ala Ala Ala Val Arg Leu Xaa
1               5                   10                  15

Xaa

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (19)..(21)
<223> OTHER INFORMATION: A non-standard amino acid residue
<220> FEATURE:
<223> OTHER INFORMATION: C-term NH2

<400> SEQUENCE: 34

His Ala Pro Gly Thr Phe Thr Ser Asp Leu Ser Lys Gln Leu Glu Glu
1               5                   10                  15

Glu Ala Xaa Xaa Xaa
            20

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (15)..(16)
<223> OTHER INFORMATION: A non-standard amino acid residue
<220> FEATURE:
<223> OTHER INFORMATION: C-term NH2

```
<400> SEQUENCE: 35

His Ala Pro Gly Thr Phe Thr Ser Asp Ala Ala Ala Arg Leu Xaa Xaa
1               5                   10                  15

<210> SEQ ID NO 36
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: His, absent or any non-standard amino acid
      structure "Y1"
<220> FEATURE:
<221> NAME/KEY: MOD_RES
<222> LOCATION: (2)..(2)
<223> OTHER INFORMATION: Gly, Ala, D-Ala or Aib
<220> FEATURE:
<221> NAME/KEY: MOD_RES
<222> LOCATION: (3)..(3)
<223> OTHER INFORMATION: Gly, Ala, D-Ala, Aib, Glu, Pro or any
      non-standard amino acid structure "Y1"
<220> FEATURE:
<221> NAME/KEY: MOD_RES
<222> LOCATION: (14)..(14)
<223> OTHER INFORMATION: Met or Leu
<220> FEATURE:
<221> NAME/KEY: MOD_RES
<222> LOCATION: (24)..(24)
<223> OTHER INFORMATION: A non-standard amino acid residue
<220> FEATURE:
<221> NAME/KEY: MOD_RES
<222> LOCATION: (25)..(25)
<223> OTHER INFORMATION: Trp or Phe
<220> FEATURE:
<221> NAME/KEY: MOD_RES
<222> LOCATION: (28)..(28)
<223> OTHER INFORMATION: A non-standard amino acid residue
<220> FEATURE:
<221> NAME/KEY: misc_feature
<222> LOCATION: (29)..(39)
<223> OTHER INFORMATION: This region may encompass "Gly Gly" or "Gly Gly
      Pro Ser Ser Gly Ala Pro Pro Pro Ser" and is 2 to 11 residues
      in length or is absent
<220> FEATURE:
<223> OTHER INFORMATION: C-term OH or NH2

<400> SEQUENCE: 36

Xaa Xaa Xaa Gly Thr Phe Thr Ser Asp Leu Ser Lys Gln Xaa Glu Glu
1               5                   10                  15

Glu Ala Val Arg Leu Phe Ile Xaa Xaa Leu Lys Xaa Gly Gly Pro Ser
                20                  25                  30

Ser Gly Ala Pro Pro Pro Ser
            35

<210> SEQ ID NO 37
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: His, absent or a non-standard amino acid
      structure "Y1"
<220> FEATURE:
<221> NAME/KEY: MOD_RES
<222> LOCATION: (2)..(2)
```

```
<223> OTHER INFORMATION: Gly, Ala, D-Ala or Aib
<220> FEATURE:
<221> NAME/KEY: MOD_RES
<222> LOCATION: (3)..(3)
<223> OTHER INFORMATION: Gly, Ala, D-Ala, Aib, Glu, Pro or a
      non-standard amino acid structure "Y1"
<220> FEATURE:
<221> NAME/KEY: MOD_RES
<222> LOCATION: (14)..(14)
<223> OTHER INFORMATION: Met or Leu
<220> FEATURE:
<221> NAME/KEY: MOD_RES
<222> LOCATION: (24)..(24)
<223> OTHER INFORMATION: A non-standard amino acid residue connected to
      position 28 by an alkenylenyl or alkylenyl bridge
<220> FEATURE:
<221> NAME/KEY: MOD_RES
<222> LOCATION: (25)..(25)
<223> OTHER INFORMATION: Trp or Phe
<220> FEATURE:
<221> NAME/KEY: MOD_RES
<222> LOCATION: (28)..(28)
<223> OTHER INFORMATION: A non-standard amino acid residue connected to
      position 24 by an alkenylenyl or alkylenyl bridge
<220> FEATURE:
<221> NAME/KEY: misc_feature
<222> LOCATION: (29)..(39)
<223> OTHER INFORMATION: This region may encompass "Gly Gly" or "Gly Gly
      Pro Ser Ser Gly Ala Pro Pro Pro Ser" and is 2 to 11 residues
      in length or is absent
<220> FEATURE:
<223> OTHER INFORMATION: C-term OH or NH2

<400> SEQUENCE: 37

Xaa Xaa Xaa Gly Thr Phe Thr Ser Asp Leu Ser Lys Gln Xaa Glu Glu
1               5                   10                  15

Glu Ala Val Arg Leu Phe Ile Xaa Xaa Leu Lys Xaa Gly Gly Pro Ser
            20                  25                  30

Ser Gly Ala Pro Pro Pro Ser
        35

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: A non-standard amino acid residue connected to
      position 28 by an alkenylenyl or alkylenyl bridge
<220> FEATURE:
<221> NAME/KEY: MOD_RES
<222> LOCATION: (28)..(28)
<223> OTHER INFORMATION: A non-standard amino acid residue connected to
      position 24 by an alkenylenyl or alkylenyl bridge
<220> FEATURE:
<223> OTHER INFORMATION: C-term NH2

<400> SEQUENCE: 38

His Ala Pro Gly Thr Phe Thr Ser Asp Leu Ser Lys Gln Leu Glu Glu
1               5                   10                  15

Glu Ala Val Arg Leu Phe Ile Xaa Phe Leu Lys Xaa
            20                  25
```

```
<210> SEQ ID NO 39
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: A non-standard amino acid residue connected to
      position 28 by an alkenylenyl or alkylenyl bridge
<220> FEATURE:
<221> NAME/KEY: MOD_RES
<222> LOCATION: (28)..(28)
<223> OTHER INFORMATION: A non-standard amino acid residue connected to
      position 24 by an alkenylenyl or alkylenyl bridge
<220> FEATURE:
<223> OTHER INFORMATION: C-term NH2

<400> SEQUENCE: 39

His Ala Pro Gly Thr Phe Thr Ser Asp Leu Ser Lys Gln Leu Glu Glu
1               5                   10                  15

Glu Ala Val Arg Leu Phe Ile Xaa Phe Leu Lys Xaa
            20                  25

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: A non-standard amino acid residue connected to
      position 28 by an alkenylenyl or alkylenyl bridge
<220> FEATURE:
<221> NAME/KEY: MOD_RES
<222> LOCATION: (28)..(28)
<223> OTHER INFORMATION: A non-standard amino acid residue connected to
      position 24 by an alkenylenyl or alkylenyl bridge
<220> FEATURE:
<223> OTHER INFORMATION: C-term NH2

<400> SEQUENCE: 40

His Ala Pro Gly Thr Phe Thr Ser Asp Leu Ser Lys Gln Leu Glu Glu
1               5                   10                  15

Glu Ala Val Arg Leu Phe Ile Xaa Phe Leu Lys Xaa
            20                  25

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term NH2
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: A non-standard amino acid residue connected to
      position 28 by an alkenylenyl or alkylenyl bridge
<220> FEATURE:
<221> NAME/KEY: MOD_RES
<222> LOCATION: (28)..(28)
<223> OTHER INFORMATION: A non-standard amino acid residue connected to
      position 24 by an alkenylenyl or alkylenyl bridge
<220> FEATURE:
<223> OTHER INFORMATION: C-term NH2

<400> SEQUENCE: 41

His Ala Pro Gly Thr Phe Thr Ser Asp Leu Ser Lys Gln Leu Glu Glu
 1               5                  10                  15

Glu Ala Val Arg Leu Phe Ile Xaa Phe Leu Lys Xaa
                20                  25

<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: A non-standard amino acid residue connected to
      position 28 by an alkenylenyl or alkylenyl bridge
<220> FEATURE:
<221> NAME/KEY: MOD_RES
<222> LOCATION: (28)..(28)
<223> OTHER INFORMATION: A non-standard amino acid residue connected to
      position 24 by an alkenylenyl or alkylenyl bridge
<220> FEATURE:
<223> OTHER INFORMATION: C-term NH2

<400> SEQUENCE: 42

His Ala Pro Gly Thr Phe Thr Ser Asp Leu Ser Lys Gln Leu Glu Glu
 1               5                  10                  15

Glu Ala Val Arg Leu Phe Ile Xaa Phe Leu Lys Xaa
                20                  25

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: A non-standard amino acid residue connected to
```

```
      position 28 by an alkenylenyl or alkylenyl bridge
<220> FEATURE:
<221> NAME/KEY: MOD_RES
<222> LOCATION: (28)..(28)
<223> OTHER INFORMATION: A non-standard amino acid residue connected to
      position 24 by an alkenylenyl or alkylenyl bridge
<220> FEATURE:
<223> OTHER INFORMATION: C-term NH2

<400> SEQUENCE: 43

His Ala Pro Gly Thr Phe Thr Ser Asp Leu Ser Lys Gln Leu Glu Glu
1               5                   10                  15

Glu Ala Val Arg Leu Phe Ile Xaa Phe Leu Lys Xaa
            20                  25

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: A non-standard amino acid residue connected to
      position 28 by an alkenylenyl or alkylenyl bridge
<220> FEATURE:
<221> NAME/KEY: MOD_RES
<222> LOCATION: (28)..(28)
<223> OTHER INFORMATION: A non-standard amino acid residue connected to
      position 24 by an alkenylenyl or alkylenyl bridge
<220> FEATURE:
<223> OTHER INFORMATION: C-term NH2

<400> SEQUENCE: 44

His Ala Pro Gly Thr Phe Thr Ser Asp Leu Ser Lys Gln Leu Glu Glu
1               5                   10                  15

Glu Ala Val Arg Leu Phe Ile Xaa Phe Leu Lys Xaa
            20                  25

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: A non-standard amino acid residue connected to
      position 28 by an alkenylenyl or alkylenyl bridge
<220> FEATURE:
<221> NAME/KEY: MOD_RES
<222> LOCATION: (28)..(28)
<223> OTHER INFORMATION: A non-standard amino acid residue connected to
      position 24 by an alkenylenyl or alkylenyl bridge
<220> FEATURE:
<223> OTHER INFORMATION: C-term NH2
```

```
<400> SEQUENCE: 45

His Ala Pro Gly Thr Phe Thr Ser Asp Leu Ser Lys Gln Leu Glu Glu
1               5                   10                  15

Glu Ala Val Arg Leu Phe Ile Xaa Phe Leu Lys Xaa
            20                  25

<210> SEQ ID NO 46
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: A non-standard amino acid residue connected to
      position 28 by an alkenylenyl or alkylenyl bridge
<220> FEATURE:
<221> NAME/KEY: MOD_RES
<222> LOCATION: (28)..(28)
<223> OTHER INFORMATION: A non-standard amino acid residue connected to
      position 24 by an alkenylenyl or alkylenyl bridge
<220> FEATURE:
<223> OTHER INFORMATION: C-term NH2

<400> SEQUENCE: 46

His Ala Pro Gly Thr Phe Thr Ser Asp Leu Ser Lys Gln Leu Glu Glu
1               5                   10                  15

Glu Ala Val Arg Leu Phe Ile Xaa Phe Leu Lys Xaa
            20                  25

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (4)..(4)
<223> OTHER INFORMATION: A non-standard amino acid residue
<220> FEATURE:
<221> NAME/KEY: MOD_RES
<222> LOCATION: (8)..(8)
<223> OTHER INFORMATION: A non-standard amino acid residue
<220> FEATURE:
<223> OTHER INFORMATION: C-term Resin

<400> SEQUENCE: 47

Leu Phe Ile Xaa Phe Leu Lys Xaa
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
```

```
<220> FEATURE:
<221> NAME/KEY: MOD_RES
<222> LOCATION: (4)..(4)
<223> OTHER INFORMATION: A non-standard amino acid residue connected to
      position 8 by an alkenylenyl or alkylenyl bridge
<220> FEATURE:
<221> NAME/KEY: MOD_RES
<222> LOCATION: (8)..(8)
<223> OTHER INFORMATION: A non-standard amino acid residue connected to
      position 4 by an alkenylenyl or alkylenyl bridge
<220> FEATURE:
<223> OTHER INFORMATION: C-term Resin

<400> SEQUENCE: 48

Leu Phe Ile Xaa Phe Leu Lys Xaa
1               5

<210> SEQ ID NO 49
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: A non-standard amino acid residue connected to
      position 28 by an alkenylenyl or alkylenyl bridge
<220> FEATURE:
<221> NAME/KEY: MOD_RES
<222> LOCATION: (28)..(28)
<223> OTHER INFORMATION: A non-standard amino acid residue connected to
      position 24 by an alkenylenyl or alkylenyl bridge
<220> FEATURE:
<223> OTHER INFORMATION: C-term resin

<400> SEQUENCE: 49

His Ala Pro Gly Thr Phe Thr Ser Asp Leu Ser Lys Gln Leu Glu Glu
1               5                   10                  15

Glu Ala Val Arg Leu Phe Ile Xaa Phe Leu Lys Xaa
            20                  25
```